(12) United States Patent
Abrahmsén et al.

(10) Patent No.: US 10,556,933 B2
(45) Date of Patent: Feb. 11, 2020

(54) POLYPEPTIDE LIBRARIES WITH A PREDETERMINED SCAFFOLD

(71) Applicant: Affibody AB, Solna (SE)

(72) Inventors: Lars Abrahmsén, Bromma (SE); Nina Herne, Stockholm (SE); Christofer Lendel, Farsta (SE); Joachim Feldwisch, Tyresö (SE)

(73) Assignee: AFFIBODY AB, Solna (SE)

( * ) Notice: Subject to any disclaimer, the term of this patent is extended or adjusted under 35 U.S.C. 154(b) by 373 days.

(21) Appl. No.: 15/238,184

(22) Filed: Aug. 16, 2016

(65) Prior Publication Data

US 2017/0008936 A1     Jan. 12, 2017

Related U.S. Application Data

(62) Division of application No. 12/735,069, filed as application No. PCT/EP2008/068168 on Dec. 22, 2008, now Pat. No. 9,469,670.
(Continued)

(30) Foreign Application Priority Data

Dec. 21, 2007   (EP) .................................. 07150394

(51) Int. Cl.
    *C40B 40/10*    (2006.01)
    *C07K 14/31*    (2006.01)
    (Continued)

(52) U.S. Cl.
    CPC .............. *C07K 14/31* (2013.01); *C07K 1/047* (2013.01); *C12N 15/1037* (2013.01);
    (Continued)

(58) Field of Classification Search
None
See application file for complete search history.

(56) References Cited

U.S. PATENT DOCUMENTS 5,831,012 A     11/1998   Nilsson et al.
6,534,628 B1     3/2003   Nilsson et al.
(Continued)

FOREIGN PATENT DOCUMENTS

EP     2077272 A1     7/2009
WO     9101743 A1     2/1991
(Continued)

OTHER PUBLICATIONS

Alvarez, et al. "Biology of Platelet-Derived Growth Factor and its Involvement in Disease" Mayo Clin Proc, Sep. 2006; vol. 81, No. 9, pp. 1241-1257.
(Continued)

*Primary Examiner* — Christian C Boesen
(74) *Attorney, Agent, or Firm* — Cantor Colburn LLP

(57) ABSTRACT

Populations of polypeptide variants based on a common scaffold, each polypeptide in the population comprising the scaffold amino acid sequence EXXXAXXEIX XLPN-LTXXQX XAFIXKLXDD PSQSSELLSE AKKLNDSQ (SEQ ID NO: 1) or AKYAKEXXXAXX EIXXLPNLTX XQXXAFIXKL XDDPSQSSEL LSEAKKLNDS Q (SEQ ID NO: 2), wherein each X individually corresponds to an amino acid residue which is varied in the population are disclosed. Also populations of polynucleotides, wherein each member encodes a member of a polypeptide population are disclosed. Furthermore, combinations of such polypeptide populations and such polynucleotide populations are disclosed, wherein each member of polypeptide population is physically or spatially associated with the polynucleotide encoding that member via means for genotype-phenotype coupling.

20 Claims, 10 Drawing Sheets

Specification includes a Sequence Listing.

Related U.S. Application Data

(60) Provisional application No. 61/009,171, filed on Dec. 26, 2007.

(51) Int. Cl.
 *C12N 15/10* (2006.01)
 *C07K 1/04* (2006.01)
 *G01N 33/68* (2006.01)

(52) U.S. Cl.
 CPC ..... *C12N 15/1041* (2013.01); *C12N 15/1044* (2013.01); *C12N 15/1075* (2013.01); *G01N 33/6845* (2013.01); *C40B 40/10* (2013.01); *G01N 2333/31* (2013.01)

(56) References Cited

U.S. PATENT DOCUMENTS

| | | |
|---|---|---|
| 6,602,977 B1 | 8/2003 | Ljungqvist et al. |
| 6,740,734 B1 | 5/2004 | Nilsson et al. |
| 7,993,650 B2 | 8/2011 | Carlsson et al. |
| 8,124,725 B2 | 2/2012 | Marino et al. |
| 2009/0180954 A1 | 7/2009 | Marino et al. |
| 2009/0191124 A1 | 7/2009 | Marino et al. |
| 2010/0286366 A1 | 11/2010 | Abrahmsen et al. |
| 2011/0021424 A1 | 1/2011 | Lindborg et al. |

FOREIGN PATENT DOCUMENTS

| | | |
|---|---|---|
| WO | 9200091 A1 | 1/1992 |
| WO | 9519374 A1 | 7/1995 |
| WO | 2005003156 A1 | 1/2005 |
| WO | 2005097202 A2 | 10/2005 |
| WO | 2006092338 A2 | 9/2006 |
| WO | 2007065635 A1 | 6/2007 |
| WO | 2009019117 A1 | 2/2009 |
| WO | 2009077175 A1 | 6/2009 |
| WO | 2009077569 A1 | 6/2009 |
| WO | 2009080810 A1 | 7/2009 |
| WO | 2009080811 A1 | 7/2009 |

OTHER PUBLICATIONS

Baranowska-Kortylewicz et al. "Efect of Platelet-Derived Growth Factor Receptor-β Inhibition with STI157 on Radioimmunotherapy" Cancer Research 2005, vol. 65, No. 17, Sep. 1, 2005, pp. 7824-7831.
Bohmer et al. "A Single Amino Acid Exchange Inverts Susceptibility of Related Receptor Tyrosine Kinases for the ATP Site Inhibitor STI-571*" The Journal of Biological Chemistry, 2003 vol. 278, No. 7, pp. 5148-5155.
Gronwall et al. "Selection and Characterization of Affibody Ligands Binding to Alzheimer Amyloid β Peptides" Journal of Biotechnology, 128 (2007) 162-183.
Hosse et al., "A New Generation of Protein Display Scaffolds for Molecular Recognition", Protein Science; 15 (2006); pp. 14-27.
Informational Pamphlet "Phusion® Flash, High-idelity PCR Master Mix" Finnzymes; Version 1.4; Oct. 2010; 2 Pages.
International Search Report of the International Searching Authority for International Patent Application No. PCT/EP2008/068168; International filing Date: Dec. 22, 2008; dated Apr. 27, 2009.
IPRP and Written Opinion of the International Searching Authority for International Patent Application No. PCT/EP2008/068168; International Filing Date: Dec. 22, 2008; dated Jun. 22, 2010.
Jones, et al. "Oncogenic derivatives of platelet-derived growth factor receptors" Celluar and Molecular Life Sciences, vol. 61, (2004) pp. 2912-2923.
Levitzki "PDGF receptor kinase inhibitors for the treatment of PDGF driven diseases" Cytokine & Growth Factor Reviews, vol. 15 (2004) pp. 229-235.
Lindborg et al. "Engineered High-Affinity Affibody Molecules Targeting Platelet-Derived Growth Factor Receptor β In Vivo" Journal of Molecular Biology, (2011) vol. 407, pp. 298-315.
Linhult et al. "Improving the Tolerance of a Protein A Analogue to Repeated Alkaline Exposures Using a Bypass Mutagenesis Approach" Proteins, vol. 55. pp. 407-416 (2004).
Nord et al. "A Combinatorial Library of an a-helical Bacterial Receptor Domain" Protein Engineering, vol. 8, No. 6, pp. 601-608 (1995).
Nord et al. "Binding Proteins Selected from Combinatorial Libraries of an a-helical Bacterial Receptor Domain" Nature Biotechnology, vol. 15, pp. 772-777 (1997).
Orlova et al. "Affiboyd Molecules for molecular Imaging and Therapy for Cancer" Cancer Biotherapy and Radiopharmaceuticals, vol. 22, No. 5. (2007).
Orlova et al. "Synthetic Affibody Molecules: A Novel Class of Affinity Ligands for Molecualr Imaging of HER2—Expressing Malignant Tumors" Cancer Research, vol. 67, No. 5, pp. 2178-2186 (Mar. 1, 2007).
Orlova et al. "Tumor Imaging Using a Picomolar Affinity HER2 Binding Affibody Molecule" Cancer Research, vol. 66, No. 8, pp. 4339-4348 (Apr. 15, 2006).
Ostmanet al. "PDGF Receptors as Targets in Tumor Treatment" Advances in Cancer Research, 2007, vol. 97, pp. 247-274.
Paulsson et al. "Prognostic Significance of Stromal Platelet-Derived Growth Factor β-Receptor Expression in Human Breast Cancer" The American Journal of Pathology, vol. 175, No. 1, Jul. 2009, pp. 334-341.
Pietras et al. "PDGF receptors as cancer drug targets" Cancer Cell, May 2003, vol. 3, pp. 439-443.
Rossi et al. "PDGFR expression in differential diagnosis between KIT-negative gastrointestinal stromal tumours and other primary soft-tissue tumours of the gastrointestinal tract" Histopathology 2005, vol. 46, pp. 522-531.
Shen et al. "An antibody directed against PDGF receptor β enhances the antitumor and the anti-angiogenic activies of an anti-VEGF receptor 2 antibody" Biochemical and Biophysical Research Communications 357, (2007), pp. 1141-1127.
Sörensen et al., "First-in-Human Molecular Imaging of HER2 Expressin in Breast Cancer Metastases Using the 111 In-ABY-025 Affibody Molecule", The Journal of Nuclear Medicine; 55; 2014; (pp. 730-735).
Tolmachev et al. "Radionucide Therapy of HER2-Positive Microxenografts Using A Lu-Labeled HER2-Specific Affibody Molecule" Cancer Research, vol. 67, No. 6 (Mar. 15, 2007).
Tolmachev et al., "Imaging of Platelet-Derived Growth Factor Receptor β Expression in Glioblastoma Xenografts Using Affibody Molecule 111-In-DOTA-Z09591", Journal of Nuclear Medicine, 2014, 55: 1-7; epublished on Jan. 9, 2014, as doi:10.2967/jnumed.11.
Tran et al. "Te-maEEE-ZHER2:342 an Affibody Molecule-Based Tracer for the Detection fo HER2 Expression in Malignant Tumors" bioconjugate Chemistry, vol. 18,. No. 6 pp. 1956-1964 (2007).
Wikman et al. "Selection and Characterization of HER2/neu-biding Affibiody Ligands" Protein Engineering, Design and Selection, vol. 17, No. 5, pp. 455-462 (Jun. 18, 2004).

SEQUENCE LISTING

```
<160> NUMBER OF SEQ ID NOS: 46

<210> SEQ ID NO 1
<211> LENGTH: 48
<212> TYPE: PRT
<213> ORGANISM: Artificial Sequence
<220> FEATURE:
<223> OTHER INFORMATION: Artificial population of synthetic polypeptide
      variants
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
```

<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 1

```
Glu Xaa Xaa Xaa Ala Xaa Xaa Glu Ile Xaa Xaa Leu Pro Asn Leu Thr
1               5                   10                  15

Xaa Xaa Gln Xaa Xaa Ala Phe Ile Xaa Lys Leu Xaa Asp Asp Pro Ser
            20                  25                  30

Gln Ser Ser Glu Leu Leu Ser Glu Ala Lys Lys Leu Asn Asp Ser Gln
        35                  40                  45
```

<210> SEQ ID NO 2
<211> LENGTH: 53
<212> TYPE: PRT
<213> ORGANISM: Artificial Sequence
<220> FEATURE:
<223> OTHER INFORMATION: Artificial population of synthetic polypeptide variants
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 2

```
Ala Lys Tyr Ala Lys Glu Xaa Xaa Xaa Ala Xaa Xaa Glu Ile Xaa Xaa
1               5                   10                  15

Leu Pro Asn Leu Thr Xaa Xaa Gln Xaa Xaa Ala Phe Ile Xaa Lys Leu
            20                  25                  30

Xaa Asp Asp Pro Ser Gln Ser Ser Glu Leu Leu Ser Glu Ala Lys Lys
        35                  40                  45

Leu Asn Asp Ser Gln
    50
```

```
<210> SEQ ID NO 3
<211> LENGTH: 58
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: mercaptoacetyl coupled to the N-terminus

<400> SEQUENCE: 3

Glu Ser Glu Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 4
<211> LENGTH: 59
<212> TYPE: PRT
<213> ORGANISM: Artificial Sequence
<220> FEATURE:
<223> OTHER INFORMATION: Synthetic Sequence

<400> SEQUENCE: 4

Ala Glu Ala Lys Tyr Ala Lys Glu Met Trp Ile Ala Trp Glu Glu Ile
1               5                   10                  15

Arg Asn Leu Pro Asn Leu Asn Gly Trp Gln Met Thr Ala Phe Ile Ala
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys Cys
    50                  55

<210> SEQ ID NO 5
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 5

Ala Glu Asn Lys Phe Asn Lys Glu Met Trp Ile Ala Trp Glu Glu Ile
1               5                   10                  15

Arg Asn Leu Pro Asn Leu Thr Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 6
<211> LENGTH: 123
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: misc_feature
<222> LOCATION: (25)..(33)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t
<220> FEATURE:
<221> NAME/KEY: misc_feature
<222> LOCATION: (49)..(54)
<223> OTHER INFORMATION: n is a, c, g, or t
<220> FEATURE:
<221> NAME/KEY: misc_feature
<222> LOCATION: (70)..(75)
<223> OTHER INFORMATION: n is a, c, g, or t
<220> FEATURE:
<221> NAME/KEY: misc_feature
<222> LOCATION: (79)..(84)
<223> OTHER INFORMATION: n is a, c, g, or t
<220> FEATURE:
<221> NAME/KEY: misc_feature
<222> LOCATION: (94)..(96)
<223> OTHER INFORMATION: n is a, c, g, or t
<220> FEATURE:
<221> NAME/KEY: misc_feature
<222> LOCATION: (103)..(105)
<223> OTHER INFORMATION: n is a, c, g, or t

<400> SEQUENCE: 6
gtagatgcca aatacgccaa agaannnnnn nnngcgnnnn nngagatcnn nnnnttacct      60
aacttaaccn nnnnncaann nnnngccttc atcnnnaaat tannngatga cccaagccag    120
agc                                                                 123

<210> SEQ ID NO 7
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 7
agctctgaat tactgagcga agctaaaaag ctaaatgata gccagggcgc cgaaagtaga     60
ctac                                                                 64

<210> SEQ ID NO 8
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 8
gtagtctact ttcggcgcct ggctatcatt tagcttttta gcttcgctca gtaattcaga     60
gct                                                                  63

<210> SEQ ID NO 9
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 9
aaataaatct cgaggtagat gccaaatacg ccaaag                               36
```

```
<210> SEQ ID NO 10
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 10
taaataatga gctctggctt gggtcatc                                              28

<210> SEQ ID NO 11
<211> LENGTH: 14
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (12)..(13)
<223> OTHER INFORMATION: Variant molecule

<400> SEQUENCE: 11

Met Gly Ser Ser His His His His His His Leu Gln Val Asp
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (6)..(7)
<223> OTHER INFORMATION: Variant molecule

<400> SEQUENCE: 12

Met Gly Ser Ser Leu Gln Val Asp Cys
1               5

<210> SEQ ID NO 13
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 13

Val Asp Asn Lys Phe Asn Lys Glu Leu Gly Trp Ala Ile Gly Glu Ile
1               5                   10                  15

Gly Thr Leu Pro Asn Leu Asn His Gln Gln Phe Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Artificial Sequence
<220> FEATURE:
<223> OTHER INFORMATION: Synthetic Sequence
```

```
<400> SEQUENCE: 14

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 15
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 15

Val Asp Asn Lys Phe Asn Lys Glu Lys Tyr Met Ala Tyr Gly Glu Ile
1               5                   10                  15

Arg Leu Leu Pro Asn Leu Asn His Gln Gln Val Met Ala Phe Ile Asp
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 16
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 16

Val Asp Asn Lys Phe Asn Lys Glu Lys Gly Glu Ala Val Val Glu Ile
1               5                   10                  15

Phe Arg Leu Pro Asn Leu Asn Gly Arg Gln Val Lys Ala Phe Ile Ala
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 17
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 17

Val Asp Asn Lys Phe Asn Lys Glu Leu Ile Glu Ala Ala Ala Glu Ile
1               5                   10                  15

Asp Ala Leu Pro Asn Leu Asn Arg Arg Gln Trp Asn Ala Phe Ile Lys
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 18
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 18
gtgagcggat aacaattccc ctc                                              23

<210> SEQ ID NO 19
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 19
cagcaaaaaa cccctcaaga ccc                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 20
cagcaaaaaa cccctcaaga ccc                                              23

<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 21
agataacaaa ttcaacaaag                                                  20

<210> SEQ ID NO 22
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 22
ctactttcgg cgcctgagca tcatttag                                         28

<210> SEQ ID NO 23
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 23
actttcggcg cctgagcatc atttag                                           26

<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 24
ataacaaatt caacaaagaa                                                    20

<210> SEQ ID NO 25
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 25
actttcggcg cctgagaatc atttagcttt tta                                     33

<210> SEQ ID NO 26
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 26
ctactttcgg cgcctgagaa tcatttagct tttta                                   35

<210> SEQ ID NO 27
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 27
agatgccaaa tacgccaaag aaatgcgaa                                          29

<210> SEQ ID NO 28
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 28
atgccaaata cgccaaagaa atgcgaa                                            27

<210> SEQ ID NO 29
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 29
cccaagccaa agctctgaat tgctatcaga agctaaaaag c                            41

<210> SEQ ID NO 30
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 30 gcttttttagc ttctgatagc aattcagagc tttggcttgg g                           41
```

```
<210> SEQ ID NO 31
<211> LENGTH: 102
<212> TYPE: DNA
<213> ORGANISM: Artificial Sequence
<220> FEATURE:
<223> OTHER INFORMATION: Synthetic Sequence

<400> SEQUENCE: 31
agatgccaaa tacgccaaag aaaaggggga ggcggtggtt gagatcttta ggttacctaa     60
cttaaccggg aggcaagtga aggccttcat cgcgaaatta ta                       102

<210> SEQ ID NO 32
<211> LENGTH: 102
<212> TYPE: DNA
<213> ORGANISM: Artificial Sequence
<220> FEATURE:
<223> OTHER INFORMATION: Synthetic Sequence

<400> SEQUENCE: 32
ctactttcgg cgcctggcta tcatttagct ttttagcttc gctcagtaat tcagagctct     60
ggcttgggtc atcccataat ttaaggatga aggcccgaaa tt                       102

<210> SEQ ID NO 33
<211> LENGTH: 102
<212> TYPE: DNA
<213> ORGANISM: Artificial Sequence
<220> FEATURE:
<223> OTHER INFORMATION: Synthetic Sequence

<400> SEQUENCE: 33
agatgccaaa tacgccaaag aaaagtatat ggcgtatggt gagatccggt tgttacctaa     60
cttaacccat cagcaagtta tggccttcat cgataaatta gt                       102

<210> SEQ ID NO 34
<211> LENGTH: 102
<212> TYPE: DNA
<213> ORGANISM: Artificial Sequence
<220> FEATURE:
<223> OTHER INFORMATION: Synthetic Sequence

<400> SEQUENCE: 34
ctactttcgg cgcctggcta tcatttagct ttttagcttc gctcagtaat tcagagctct     60
ggcttgggtc atccactaat ttatcgatga aggccataac tt                       102

<210> SEQ ID NO 35
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 35
agatgccaaa tacgccaaag                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
atgccaaata cgccaaagaa                                                 20
```

```
<210> SEQ ID NO 37
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 37
ctactttcgg cgcctggcta tcatttag                                        28

<210> SEQ ID NO 38
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 38
actttcggcg cctggctatc atttag                                          26

<210> SEQ ID NO 39
<211> LENGTH: 12
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (4)..(5)
<223> OTHER INFORMATION: Variant molecule
<220> FEATURE:
<221> NAME/KEY: DOMAIN
<222> LOCATION: (8)..(9)
<223> OTHER INFORMATION: albumin binding domain GA3 from Streptococcus
      sp. G148

<400> SEQUENCE: 39

Ala Gln Leu Glu Val Asp Tyr Val Ser Gln Lys Ala
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: DOMAIN
<222> LOCATION: (6)..(7)
<223> OTHER INFORMATION: First Variant Molecule
<220> FEATURE:
<221> NAME/KEY: DOMAIN
<222> LOCATION: (6)..(7)
<223> OTHER INFORMATION: Second Variant Molecule
<220> FEATURE:
<221> NAME/KEY: BINDING
<222> LOCATION: (8)..(8)
<223> OTHER INFORMATION: Albumin Binding Domain

<400> SEQUENCE: 40

Met Gly Ser Ser Leu Gln Val Asp
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: DOMAIN
<222> LOCATION: (6)..(7)
<223> OTHER INFORMATION: Variant Molecule
<220> FEATURE:
<221> NAME/KEY: DOMAIN
<222> LOCATION: (6)..(7)
<223> OTHER INFORMATION: Variant Molecule
<220> FEATURE:
<221> NAME/KEY: DOMAIN
<222> LOCATION: (8)..(8)
<223> OTHER INFORMATION: Albumin Binding Domain

<400> SEQUENCE: 41

Met Gly Ser Ser Leu Gln Val Asp
1               5

<210> SEQ ID NO 42
<211> LENGTH: 48
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 42

Glu Xaa Xaa Xaa Ala Xaa Xaa Glu Ile Xaa Xaa Leu Pro Asn Leu Asn
1               5                   10                  15

Xaa Xaa Gln Xaa Xaa Ala Phe Ile Xaa Ser Leu Xaa Asp Asp Pro Ser
            20                  25                  30

Gln Ser Ala Asn Leu Leu Ala Glu Ala Lys Lys Leu Asn Asp Ala Gln
        35                  40                  45

<210> SEQ ID NO 43
<211> LENGTH: 53
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(9)
<223> OTHER INFORMATION: Xaa can be any naturally occurring amino acid
```

```
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 43

Asn Lys Phe Asn Lys Glu Xaa Xaa Xaa Ala Xaa Xaa Glu Ile Xaa Xaa
1               5                   10                  15

Leu Pro Asn Leu Asn Xaa Xaa Gln Xaa Xaa Ala Phe Ile Xaa Ser Leu
            20                  25                  30

Xaa Asp Asp Pro Ser Gln Ser Ala Asn Leu Leu Ala Glu Ala Lys Lys
        35                  40                  45

Leu Asn Asp Ala Gln
    50

<210> SEQ ID NO 44
<211> LENGTH: 48
<212> TYPE: PRT
<213> ORGANISM: Artificial Sequence
<220> FEATURE:
<223> OTHER INFORMATION: Synthetic Sequence

<400> SEQUENCE: 44

Glu Leu Gly Trp Ala Ile Gly Glu Ile Gly Thr Leu Pro Asn Leu Thr
1               5                   10                  15

His Gln Gln Phe Arg Ala Phe Ile Leu Lys Leu Trp Asp Asp Pro Ser
            20                  25                  30

Gln Ser Ser Glu Leu Leu Ser Glu Ala Lys Lys Leu Asn Asp Ser Gln
        35                  40                  45

<210> SEQ ID NO 45
<211> LENGTH: 48
<212> TYPE: PRT
<213> ORGANISM: Artificial Sequence
<220> FEATURE:
<223> OTHER INFORMATION: Synthetic Sequence

<400> SEQUENCE: 45

Glu Lys Tyr Met Ala Tyr Gly Glu Ile Arg Leu Leu Pro Asn Leu Thr
1               5                   10                  15

His Gln Gln Val Met Ala Phe Ile Asp Lys Leu Val Asp Asp Pro Ser
            20                  25                  30

Gln Ser Ser Glu Leu Leu Ser Glu Ala Lys Lys Leu Asn Asp Ser Gln
        35                  40                  45
```

```
<210> SEQ ID NO 46
<211> LENGTH: 48
<212> TYPE: PRT
<213> ORGANISM: Artificial Sequence
<220> FEATURE:
<223> OTHER INFORMATION: Synthetic Sequence

<400> SEQUENCE: 46

Glu Lys Gly Glu Ala Val Val Glu Ile Phe Arg Leu Pro Asn Leu Thr
1               5                   10                  15

Gly Arg Gln Val Lys Ala Phe Ile Ala Lys Leu Tyr Asp Asp Pro Ser
                20                  25                  30

Gln Ser Ser Glu Leu Leu Ser Glu Ala Lys Lys Leu Asn Asp Ser Gln
            35                  40                  45
```

POLYPEPTIDE LIBRARIES WITH A PREDETERMINED SCAFFOLD

CROSS-REFERENCE TO RELATED APPLICATIONS

This application is a Divisional of U.S. application Ser. No. 12/735,069 filed Jul. 21, 2010, which is a § 371 US National Stage Application of PCT/EP2008/068168 filed Dec. 22, 2008, which claims the benefit of U.S. Provisional application Ser. No. 61/009,171 filed Dec. 26, 2007. All of these applications are incorporated by reference herein.

FIELD OF THE INVENTION

The present invention relates to novel populations of polypeptide variants based on a common scaffold. These populations can i.a. be used to provide novel binding proteins and polypeptides.

BACKGROUND

Different methods for construction of novel binding proteins have been described (Nygren P A and Uhlén M (1997) Curr Opin Struct Biol 7:463-469). One strategy has been to combine library generation and screening or selection for desired properties.

Original AFFIBODY molecules, populations of such molecules and scaffolds of such molecules have been described i.a. in WO 95/19374, the teaching of which is incorporated herein by reference.

For some applications proteins, polypeptides or AFFIBODY molecules, populations of such molecules and scaffolds with improved properties, such as alkali stability, low antigenicity, structural stability, amenability to chemical synthesis and hydrophilicity, are desired.

Alkali Stability

Production of protein pharmaceuticals and biotechnology reagents requires several purification steps to enrich for specific product while removing unwanted contaminants. Affinity purification mediated by proteinaceous affinity matrices such as monoclonal antibodies and Staphylococcal protein A (SpA) enables efficient purification in one step. However, to make this cost-efficient it is desirable to be able to properly regenerate the affinity matrices. This usually involves a procedure known as cleaning-in-place (CIP), wherein agents—often alkaline solutions—are used to elute contaminants.

Alkali stability is also required with molecular imaging tracers to be labeled with the most common SPECT nuclide technetium-99m, and to enable some other types of chemical modifications to be performed.

Low Antigenicity

Protein based pharmaceuticals, such as therapeutic monoclonal antibodies and AFFIBODY molecules, have the potential to elicit undesired immune responses in humans. The main factors contributing to immunogenicity are presence of impurities, protein aggregates, foreign epitopes e.g. new idiotopes, different Ig allotypes or non-self sequences. In addition, cross-reacting immunoglobulin (Ig) interactions will most likely increase the probability of generating a specific T-cell mediated memory immune response against the protein pharmaceutical. To minimize the risk of unwanted interaction with the immune system it is desirable to eliminate existing immune epitopes by protein engineering of the pharmaceutical.

AFFIBODY molecules are derived from staphylococcal protein A (SpA), which is a cell wall associated receptor on the surface of the Gram positive bacterium *Staphylococcal aureus*. More precisely, SpA is composed of five highly homologous domains all binding to immunoglobulins of many mammalian species including human. Each SpA domain interacts with human Igs in two different ways; either by direct binding to Fcγ including IgG1, IgG2 and IgG4 (Langone J J (1982) Adv Immunol 32:157-252), or by binding to members of the VH3 family (Silverman G J et al (1992) Int Rev Immunol 9:57-78). The common scaffold of original AFFIBODY molecules is identical to domain B of SpA with the exception of the G29A mutation, which was included to increase protein stability and to eliminate a hydroxylamine cleavage site, and the A1V mutation, introduced in a spacer region between domains (Nilsson B et al (1987), Prot Eng 1:107-113). The amino acid residues in SpA that are involved in the interaction with Fcγ and VH3 are well known and have been described in the literature (Graille M et al (2000) Proc Natl Acad Sci USA. 97:5399-5404). A molecular library of different AFFIBODY molecules was constructed by randomizing surface residues at one face of the molecule, including residues known to be involved in the interaction with Fcγ, thereby eliminating the affinity for Fcγ.

Structural Stability

One of the key factors to success for peptide and protein pharmaceuticals is the stability of the protein. Proteins showing high structural stability will most likely functionally withstand chemical modifications and proteolysis both during production as well as within the human body. Moreover, stability will influence the active shelf-life of the peptide or protein pharmaceuticals as well as the active life of the peptide or protein pharmaceutical within the human body.

Amenability to Chemical Synthesis

Researchers have traditionally obtained proteins by biological methods but chemical synthesis of peptides and small proteins is a powerful complementary strategy and is commonly used in structural biology, protein engineering and biomedical research. Chemical synthesis of proteins offers a rapid and efficient way of producing homogenous proteins free of biological contaminants such as DNA impurities and host cell proteins. Furthermore, flexibility is increased since chemical synthesis allows incorporation of unnatural amino acids, chemical modifications and introduction of biochemical and biophysical probes. The success of chemical synthesis of peptides and proteins is dependent on the amino acid sequence of the molecule in question. Certain amino acid residues show low coupling efficiency, meaning that several steps during synthesis need to be optimized which is a time-consuming process with no guaranteed success. In addition, amino acids difficult to efficiently introduce during chemical synthesis will have greater negative impact on protein yield the longer the protein sequence.

Increased Hydrophilicity

For most applications it is desirable that peptides and proteins are highly soluble showing a low tendency to aggregate. Such protein characteristics are especially important when it comes to protein pharmaceuticals. There is a strong positive correlation between protein surface hydrophobicity and low solubility and increased tendency to aggregate.

DESCRIPTION OF THE INVENTION

It is an object of the present invention to provide a population of polypeptide variants based on novel scaffolds.

These novel scaffolds have several advantages compared to known, similar scaffolds, so called original scaffolds. The advantages also apply to polypeptides obtained with the use of these novel scaffolds. These advantages will be discussed in more detail below, but some examples are given here. For example, extensive research has been performed to develop the novel polypeptide scaffolds showing high stability in an alkaline environment. One aspect of alkaline stability is stability towards deamidation of asparagines. Avoiding this reaction by increased structural rigidity or by replacing this residue also provides chemical stability that contributes to obtaining a homogeneous product, for example following production in a fermentation process or storage, where deamidation of asparagines strongly contributes to a heterogeneous mixture which is difficult to separate.

Moreover, an improved profile with regard to low antigenicity (little IgG binding) was obtained by elimination in the new scaffold sequence of the remaining affinity for immunoglobulins, mainly VH3 mediated.

Furthermore, the novel scaffolds have been engineered in such a way to show high structural stability with regard to an easily folded alpha helical structure, high melting temperature and abolishment of sites known to target proteolysis.

The original AFFIBODYmolecule scaffolds contain several amino acids that have been shown to reduce the rate and success of chemical synthesis. To have an efficient, i.e. high-throughput and high yield AFFIBODY protein production process, numerous amino acids were exchanged for residues with properties more compatible with chemical synthesis.

In order to improve hydrophilicity and solubility, hydrophobic residues on the surface of the AFFIBODY molecule scaffold have be exchanged for more hydrophilic amino acids.

Another object of the present invention is to provide a population of polynucleotides.

Another object of the present invention is to provide a combination of a polypeptide population and a polynucleotide population.

A further object of the present invention is to provide a method for selecting a desired polypeptide having an affinity for a predetermined target from a population of polypeptides.

Another object is to provide a method for isolating a polynucleotide encoding a desired polypeptide having an affinity for a predetermined target.

Another object is to provide a method for identifying a desired polypeptide having an affinity for a predetermined target.

A further object is to provide a method for selecting and identifying a desired polypeptide having an affinity for a predetermined target.

A related object is to provide a method for production of a desired polypeptide having an affinity for a predetermined target.

The populations and methods according to the invention enables the provision (including production and evaluation) of agents with an affinity for a predetermined target, through the provision of a polypeptide that is characterized by specific binding to the predetermined target.

It is also possible to provide polypeptides binding to a predetermined target that exhibit little or no non-specific binding.

It is also possible to provide polypeptides binding to a predetermined target that can readily be used as a moiety in a fusion polypeptide.

Furthermore, it is possible to provide polypeptides binding to a predetermined target that solve one or more of the known problems experienced with existing antibody reagents.

Moreover, it is possible to provide polypeptides binding to a predetermined target that are amenable to use in therapeutic and/or diagnostic applications.

It is also possible to provide polypeptides binding to a predetermined target that are easily made by chemical peptide synthesis.

Furthermore, the invention enables the identification of polypeptides binding to a predetermined target that exhibit an improved stability vis-à-vis known agents binding to the same target.

It is also possible to provide polypeptides binding to a predetermined target that exhibit low antigenicity when used in vivo in a mammal and/or that exhibit an improved biodistribution upon administration to a mammal.

These and other objects are met by the different aspects of the invention as claimed in the appended claims.

In a first aspect the invention provides a population of polypeptide variants based on a common scaffold, each polypeptide in the population comprising the scaffold amino acid sequence

```
                                         (SEQ. ID. No. 1)
EXXXAXXEIX XLPNLTXXQX XAFIXKLXDD PSQSSELLSE

AKKLNDSQ,.
``` or in some cases more preferably

```
                                         (SEQ. ID. No. 2)
AKYAKEXXXAXX EIXXLPNLTX XQXXAFIXKL XDDPSQSSEL

LSEAKKLNDS Q,.
```

In the sequences above each X individually corresponds to an amino acid residue which is varied in the population.

The population consists of a large number of variants of such polypeptide molecules. In this context a large number means a population comprising at least $1\times10^4$ unique polypeptide molecules, or at least $1\times10^6$ or at least $1\times10^8$ or at least $1\times10^{10}$, or at least $1\times10^{12}$, or at least $1\times10^{14}$ unique polypeptide molecules. However, it is necessary to use a group that is large enough to provide the desired size of the population. The "population" described herein may also be denoted "library".

It is stated above that each X individually corresponds to an amino acid residue which is varied. This means that each X may be any amino acid residue independent of the identity of any other residue denoted X in the sequence. In the scaffold amino acid sequence the different varied amino acids X may be chosen from all 20 naturally occurring amino acid residues in such a way that any of these 20 naturally occurring amino acid residues may be present at the corresponding X position in any given variant. The selection of amino acid residue in each position is more or less randomized. It is also possible to limit the group from which the different varied amino acid residues are selected to 19, 18, 17, 16 or less of the 20 naturally occurring amino acid residues. The variability in different positions may be adjusted individually, between one, meaning no randomization, up to all 20 amino acids. Random introduction of a smaller subset of amino acids may be obtained by careful selection of the deoxyribonucleotide bases introduced, for example the codons T(A/C)C may be introduced to obtain a random introduction of either serine or tyrosine at a given position in the polypeptide chain. Likewise, the codons (T/C/A/G)CC may be introduced to obtain a random introduction of phenylalanine, leucine, alanine and valine at a given position in the polypeptide chain. The skilled person is aware of many alternatives of deoxyribonucleotide base combinations that may be used to obtain different combinations of amino acids at a given position in the polypeptide chain. The set of amino acids that may appear at a given position in the polypeptide chain may also be determined by the introduction of trinucleotides during the oligonucleotide synthesis, instead of one deoxyribonucleotide base at a time.

The polypeptides comprising the scaffold amino acid sequences given above are novel AFFIBODY molecules. As such, they are derived from *Staphylococcal* protein A (SpA). In this context "derived" does not mean that the polypeptides themselves in any way necessarily directly originates from SpA. Instead it means that the scaffold has a sequence and structural resemblance to one SpA domain, where amino acids in the hydrophobic core of the three helical bundle protein are conserved.

Different modifications of, and/or additions to, the polypeptides constituting the population according to the invention may be performed in order to tailor the polypeptides to the specific use intended, without departing from the scope of the present invention. Such modifications and additions are described in more detail below, and may comprise additional amino acids comprised in the same polypeptide chain, or labels and/or therapeutic agents that are chemically conjugated or otherwise bound to the polypeptides constituting the population. In some embodiments additional amino acid residues on the C-terminal end may be preferred. These additional amino acid residues may play a role in the binding of the polypeptide, but may equally well serve other purposes, related for example to one or more of the production, purification, stabilization, coupling or detection of the polypeptide. Such additional amino acid residues may comprise one or more amino acid residues added for purposes of chemical coupling. An example of this is the addition of a cysteine residue at the very first or very last position in the polypeptide chain, i.e. at the N- or C-terminus. A cysteine residue to be used for chemical coupling may also be introduced by replacement of another amino acid on the surface of the protein domain, preferably on a portion of the surface that is not involved in target binding. Such additional amino acid residues may also comprise a "tag" for purification or detection of the polypeptide, such as a hexahistidyl (His$_6$) tag, or a "myc" tag or a "FLAG" tag for interaction with antibodies specific to the tag. The skilled person is aware of other alternatives.

The "additional amino acid residues" discussed above may also constitute one or more polypeptide domain(s) with any desired function, such as another binding function, or an enzymatic function, or a metal ion chelating function, or a fluorescent function, or mixtures thereof.

In a second aspect the invention provides a population of polynucleotides. Each polynucleotide in this population encodes a member of a population of polypeptides described above.

In a third aspect the invention provides a combination of a polypeptide population according to the invention and a polynucleotide population according to the invention wherein each member of the polypeptide population is physically or spatially associated with the polynucleotide encoding that member via means for genotype-phenotype coupling. This physical or spatial association will be more or less strict, depending on the system used.

The means for genotype-phenotype coupling may comprise a phage display system. Phage display systems are well-known to the skilled person, and is, for example, described in Smith G P (1985) Science 228:1315-1317 and Barbas C F et al (1991) Proc Natl Acad Sci USA 88:7978-7982.

Furthermore, the means for genotype-phenotype coupling may comprise a cell surface display system. The cell surface display system may comprise prokaryotic cells, such as Gram$^+$ cells, or eukaryotic cells, such as yeast cells. Cell surface display systems are well-known to the skilled person. Prokaryotic systems are, for example, described in Francisco J A et al (1993) Proc Natl Acad Sci USA 90:10444-10448 and Lee S Y et al (2003) Trends Biotechnol 21:45-52. Eukaryotic systems are, for example, described in Boder E T et al (1997) Nat Biotechnol 15:553-557 and Gai S A et al (2007) Curr Opin Struct Biol 17:467-473.

Furthermore, the means for genotype-phenotype coupling may comprise a cell free display system. The cell free display system may comprise a ribosome display system, or an in vitro compartmentalization display system, or a system for cis display, or a microbead display system. Ribosome display systems are well-known to the skilled person, and are, for example, described in Mattheakis L C et al (1994) Proc Natl Acad Sci USA 91:9022-9026 and Zahnd C et al (2007) Nat Methods 4:269-279. In vitro compartmentalization systems are well-known to the skilled person, and are, for example, described in Sepp A et al (2002) FEBS Lett 532:455-458. Cis display systems are well-known to the skilled person, and are, for example, described in Odegrip R et al (2004) Proc Natl Acad Sci USA 101:2806-2810. Microbead display systems are well-known to the skilled person, and are, for example, described in Nord O et al (2003) J Biotechnol 106:1-13.

Furthermore, the means for genotype-phenotype coupling may comprise a non-display system such as the protein-fragment complementation assay (PCA). PCA systems are well-known to the skilled person, and are, for example, described in Koch H et al (2006) J Mol Biol 357:427-441.

In a fourth aspect the invention provides a method for selecting a desired polypeptide having an affinity for a predetermined target from a population of polypeptides, comprising the steps:

(a) providing a population of polypeptides as described above;

(b) bringing the population of polypeptides into contact with the predetermined target under conditions that enable specific interaction between the target and at least one desired polypeptide having an affinity for the target; and (c) selecting, on the basis of said specific interaction, the at least one desired polypeptide from the remaining population of polypeptides.

This method is below called the selection method according to the invention.

Step (a) may comprise the preparatory steps of providing a population of polynucleotides and expressing said population of polynucleotides to yield said population of polypeptides. The means for yielding a population of polypeptides varies depending on the display system used and examples of such means may be found in the genotype-phenotype references above. Each member of said population of polypeptides used in the selection method according to the invention may physically be associated with the polynucleotide encoding that member via means for genotype-phenotype coupling. The means for genotype-phenotype coupling may be one of those discussed above.

Step (b) comprises the steps of bringing the population of polypeptides into contact with the predetermined target under conditions that enable specific interaction between the target and at least one desired polypeptide having an affinity for the target. The range of conditions applicable is determined by the robustness of the target, the robustness of the display system, and by the desired properties of the interaction with the target. For example a specific method of separating the interaction such as acidification to a predetermined pH may be desired. The skilled person knows what experiments are required to determine suitable conditions.

Step (c) comprises the selection of at least one polypeptide. The means for selection of desired polypeptide from the remaining population, based on the specific interaction between the predetermined target and at least one desired polypeptide having affinity for the target varies depending on the display system used and may be found in the genotype-phenotype references above. For example, the in vitro display selection systems are cell free in contrast to systems such as phage display and the protein fragment compartmentalization assay.

In a fifth aspect the invention provides a method for isolating a polynucleotide encoding a desired polypeptide having an affinity for a predetermined target, comprising the steps:
  selecting said desired polypeptide and the polynucleotide encoding it from a population of polypeptides using the selection method according to the invention; and
  isolating the thus separated polynucleotide encoding the desired polypeptide.

This method is below called the isolation method according to the invention.

The separation of the polynucleotide from the polypeptide may be done differently depending on the display system used for selection. For example, in the cell free display systems such as cis display and ribosome display the polynucleotide or the corresponding mRNA is retrieved through efficient elution from the polypeptide using means described in the genotype-phenotype references above.

The isolation of the polynucleotide may be done by different methods depending on the display system used for selection. In most of the above described selection systems, for example the protein fragment complementation assay, the polynucleotide can be directly isolated by specific PCR amplification using appropriate oligonucleotides. Exceptionally, as in ribosome display, the polynucleotide can be isolated from the corresponding mRNA using reverse transcription. The various means for isolation of the polynucleotide may be found in the genotype-phenotype references above.

In a sixth aspect the invention provides a method for identifying a desired polypeptide having an affinity for a predetermined target, comprising the steps:
  isolating a polynucleotide encoding said desired polypeptide using the isolation method according to the invention; and
  sequencing the polynucleotide to establish by deduction the amino acid sequence of said desired polypeptide.

The sequencing of the polynucleotide may be done according to standard procedures well-known to the skilled person.

In a seventh aspect the invention provides a method for selecting and identifying a desired polypeptide having an affinity for a predetermined target from a population of polypeptides, comprising the steps:
  (a) synthesizing each member of the population of polypeptides on a separate carrier or bead;
  (b) selecting or enriching the carriers or beads based on the interaction of the polypeptide with the predetermined target; and
  (c) identifying the polypeptide by protein characterization methodology. In step (c), it is for example possible to use mass spectrometric analysis.

This method is below called the selection and identification method according to the invention.

In an eighth aspect the invention provides a method for production of a desired polypeptide having an affinity for a predetermined target, comprising the steps:
  selecting and identifying a desired polypeptide using the selection method according to the invention or the selection and identification method according to the invention; and
  producing said desired polypeptide.

This method is below called the production method according to the invention.

In the production method according to the invention the production may be carried out using recombinant expression of a polynucleotide encoding the desired polypeptide. The production may also be carried out using chemical synthesis of the desired polypeptide de novo.

In a ninth aspect the invention provides a method for production of a desired polypeptide having an affinity for a predetermined target, comprising the steps:
  (a1) isolating a polynucleotide encoding said desired polypeptide using the isolation method according to the invention; or
  (a2) backtranslating a polypeptide identified using the selection and identification method according to the invention; and
  (b) expressing the thus isolated polynucleotide to produce said desired polypeptide,
wherein step (b) is performed either after step (a1) or step (a2).

The expression of the polynucleotide may be done in any suitable expression host known to the skilled person such as but not limited to bacterial cells, yeast cells, insect cells or mammalian cells.

Expressions like "binding affinity for a predetermined target", "binding to a predetermined target" and the like refer to a property of a polypeptide which may be directly measured through the determination of the affinity constants i.e. the amount of polypeptide that associates and dissociates at a given antigen concentration. Different methods can be used to characterize the molecular interaction, such as, but not limited to, competition analysis, equilibrium analysis and microcalorimetric analysis, and real-time interaction analysis based on surface plasmon resonance interaction (for example using a BIACORE instrument). These methods are well-known to the skilled person and are described, for example, in Neri D et al (1996) Tibtech 14:465-470 and Jansson M et al (1997) J Biol Chem 272:8189-8197.

The inventors of the present invention have found that a polypeptide binding to a predetermined target, obtained by any of the above mentioned methods may exhibit one or more surprising advantage(s), in comparison with known polypeptides that bind to the same target, while retaining the capacity of those previously known polypeptides to bind the target. Non-limiting examples of such advantages are as follows:
  A polypeptide, binding to a predetermined target and obtained by any of the above mentioned methods, comprises fewer amino acid residues that could cause problems, such as low yield and success rate, in chemical synthesis of the polypeptide sequence, such as asparagine, arginine, aspartic acid and methionine.

A polypeptide, binding to a predetermined target and obtained by any of the above mentioned methods, comprises fewer amino acid residues that confer surface hydrophobicity. This implies fewer problems with low solubility and aggregation. Without wishing to be bound by theory, it is also currently believed that the more hydrophilic characteristics act to shift the biodistribution of the polypeptide upon administration to a host, from a hepatobiliary pathway (excretion through the liver) towards a more desired renal pathway (excretion through the kidneys).

A polypeptide, binding to a predetermined target and obtained by any of the above mentioned methods, comprises fewer amino acid residues that are associated with polypeptide stability problems, such as methionine, asparagine and the dipeptide asparagine-proline. Methionine is susceptible to oxidation, asparagine is susceptible to deamidation and the asparagine-proline bond is susceptible to acid cleavage, and they therefore contribute to non-homogeneity of the final product.

A polypeptide, binding to a predetermined target and obtained by any of the above mentioned methods, lacks amino acid residues that, in a similar sequence context, have been found to increase the interaction with immunoglobulins containing a heavy chain variable domain from VH3 (Silverman G J (1992) supra). Without wishing to be bound by theory, it is currently believed that the replacement of such amino acid residues in a polypeptide, binding to a predetermined target and obtained by any of the above mentioned methods, reduces the antigenicity of the polypeptide upon administration of the same to a host.

Among the advantages of the inventive scaffold, alkaline stability, low antigenicity, structural stability, improved properties for chemical synthesis and/or increased hydrophilicity are among the most important.

Polypeptides, binding to a predetermined target and obtained by any of the above mentioned methods, may be used as detection reagents, capture reagents, separation reagents, diagnostic agents for diagnostics in vivo or in vitro, as therapeutic agents in their own right or as means for targeting other therapeutic and/or diagnostic agents to the predetermined target. Methods that employ the polypeptides according to the invention in vitro may be performed in different formats, such as in microtiter plates, in protein arrays, on biosensor surfaces, on tissue sections, and so on.

The modifications discussed above for the polypeptides constituting the population according to the invention are also applicable to the polypeptides obtained by any of the above mentioned methods.

Polypeptides according to the invention may be produced by any known means, including chemical synthesis or expression in different prokaryotic or eukaryotic hosts, including plants and transgenic animals.

The invention will now be illustrated in detail through the description of experiments conducted in accordance therewith. The examples which follow are not to be interpreted as limiting. In the examples, reference is made to the appended figures.

EXAMPLES

Figure 1:
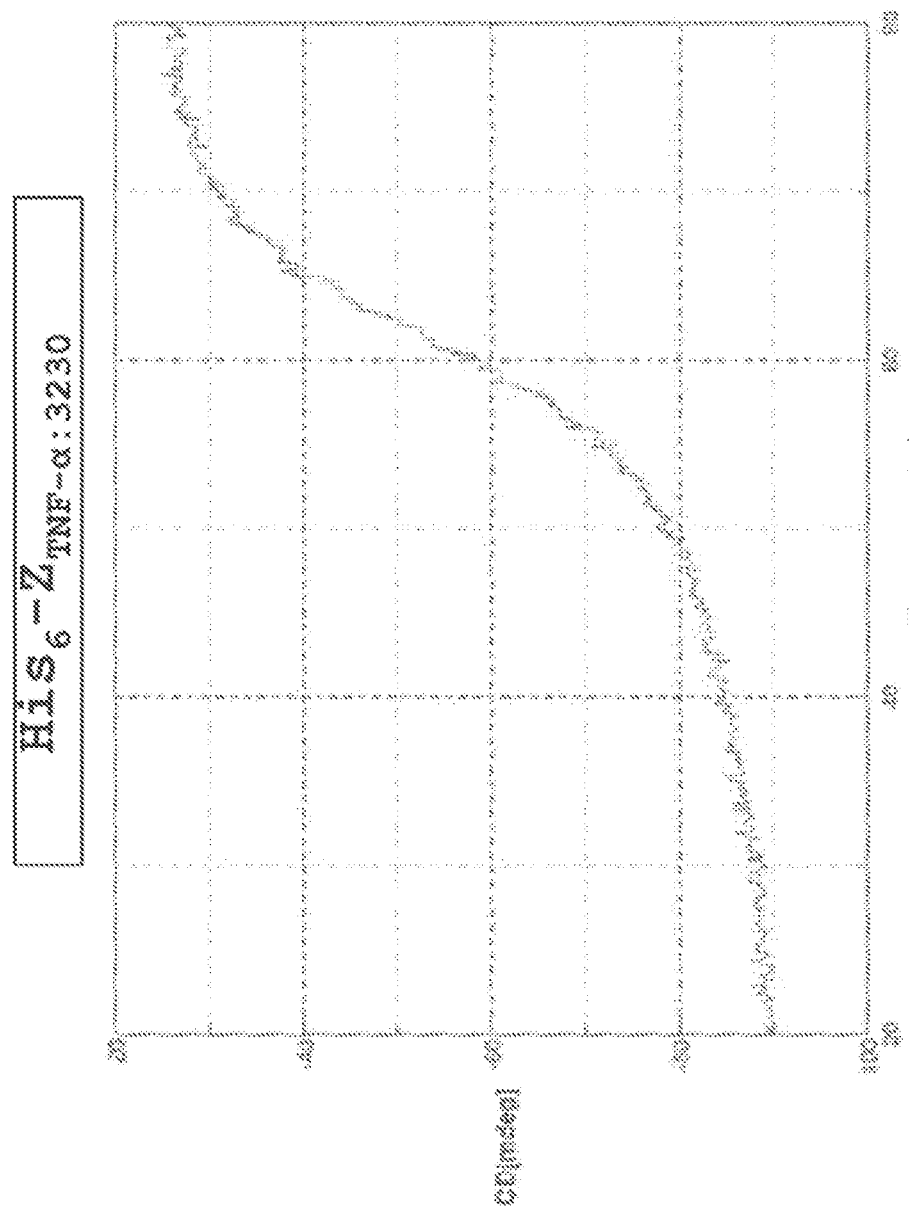
FIG. 1 shows result obtained from CD measurements, using Jasco J-810 spectro polarimeter. The variable temperature measurement of $His_6$-$Z_{TNF-\alpha:3230}$ was performed at 0.5 mg/ml in PBS buffer. The absorbance was measured at 221 nm from 20 to 80° C., with a temperature slope of 5° C./min. A cell with an optical path-length of 1 mm was used. The melting temperature (Tm) of $His_6$-$Z_{TNF-\alpha:3230}$ was determined from the variable temperature measurement.

Example 1—Construction of a Combinatorial Polypeptide Library

A combinatorial library of polypeptides was constructed essentially as described in Grönwall C et al (2007) J Biotechnol 128:162-183, by PCR amplification of a 123-nucleotide template oligonucleotide with certain degenerate codons (5'-GTA GAT GCC AAA TAC GCC AAA GAA NNN NNN NNN GCG NNN NNN GAG ATC NNN NNN TTA CCT AAC TTA ACC NNN NNN CAA NNN NNN GCC TTC ATC NNN AAA TTA NNN GAT GAC CCA AGC CAG AGC-3' SEQ ID No. 6) encoding helices 1 and 2 of the Staphylococcus aureus protein A-derived protein Z (Nilsson et al (1987), supra), with point mutations N3A, F5Y, N6A, N23T and S33K. The PCR amplification was performed using the primers AFFI-1364 and AFFI-1365 with an Xho I site and a Sac I site, respectively, underlined in Table 1.

The resulting gene fragment encoding the library was restricted with Xho I and Sac I. Subsequently, the library-encoding gene fragment was ligated into an Xho I- and Sac I-restricted phagemid vector adopted for phage display denoted pAY2016, essentially based on the phagemid vector pAffi1 (Grönwall C et al (2007), supra), in frame with amino acid residues 41-58 of protein Z, encoding helix 3 with point mutations A42S, N43E, A46S and A54S. Helix 3 was constructed by annealing of the two complementary oligonucleotides AFFI-1333 and AFFI-1334 (Table 1).

The resulting library vector was electroporated into *Escherichia coli* strain RR1ΔM15 (Ruther U (1982) Nucl Acids Res 10:5765-5772), yielding a library of $2.4 \times 10^{10}$ members.

Preparation of phage stocks from the library was performed using standard procedures involving M13K07 helper phage (New England Biolabs, Beverly, Mass., USA), routinely yielding phage titers of approximately $10^{11}$ cfu per ml cultivation.

TABLE 1

List of oligonucleotides

| Name | Sequence 5'-3' |
|---|---|
| AFFI-1333 | AGCTCTGAATTACTGAGCGAAGCTAAAAAGCTAAATGAT AGCCAGGCGCCGAAAGTAGACTAC (SEQ ID No. 7) |
| AFFI-1334 | GTAGTCTACTTTCGGCGCCTGGCTATCATTTAGCTTTTT AGCTTCGCTCAGTAATTCAGAGCT (SEQ ID No. 8) |
| AFFI-1364 | AAATAAAT<u>CTCGAG</u>GTAGATGCCAAATACGCCAAAG (SEQ ID No. 9) |
| AFFI-1365 | TAAATAAT<u>GAGCTC</u>TGGCTTGGGTCATC (SEQ ID No. 10) |

Example 2—Phage Display Selection and Characterization of Human HER2 Binding Polypeptide Variants Summary Biotinylated HER2 protein is used as target in phage display selections using the library constructed in Example 1. Selections are carried out using a variety of conditions in order to maximize the likelihood of obtaining molecules having a high affinity for HER2. After elution of selected phages, the corresponding expressed proteins are tested for affinity to HER2 in an ELISA setup. Positive clones are identified and sequenced, and the predicted amino acid sequences of the corresponding polypeptides and their HER2 binding motifs are deduced, which yields a large number of sequences of HER2 binding molecules.

Biotinylation of HER2

Lyophilized human HER2 protein (R&D Systems, #1129-ER) is dissolved in PBS (2.68 mM KCl, 1.47 mM $KH_2PO_4$, 137 mM NaCl, 8.1 mM $Na_2HPO_4$, pH 7.4) to a final concentration of 10 mg/ml. EZ-link Sulfo-NHS-LC-Biotin (Pierce, #21335) is dissolved in water to a final concentration of 1 mg/ml and a 5 and 30 fold molar excess is added to 500 μg HER2 in a total volume of 0.5 ml. The mixtures are incubated at room temperature (RT) for 30 min. Unbound biotin is removed by dialyzing against PBS using a dialysis cassette (Slide-A-Lyser, 10 kDa; Pierce).

Phage Display Selection

In total, five rounds of selection are carried out, using increasingly stringent conditions, such as decreasing HER2 concentration and increasing numbers of washes. Three initial rounds are performed, chiefly with a view to establish a suitable selection protocol. Selection is then carried out for two more cycles using the combinations of selection buffer, target concentration and solid support that are listed in Table 2.

TABLE 2

Selection conditions for HER2 selection

| Sample name | | Selection buffer supplement | Target conc. (nM) | Streptavidin beads (μg) |
|---|---|---|---|---|
| Cycle 4 | A | Gelatin | 20 | 100 |
| | B | Gelatin | 10 | 100 |
| | C | BSA | 5 | 100 |
| | D | BSA | 2.5 | 100 |
| Cycle 5 | A | Gelatin | 10 | 50 |
| | B | Gelatin | 5 | 50 |
| | C | BSA | 1 | 50 |
| | D | BSA | 0.5 | 50 |

All tubes and beads (DYNABEADS M-280 Streptavidin, #112.06; Dynal) used in the selection procedure are pre-blocked in TPBSB (5%) (0.05% Tween20, 5% bovine serum albumin (BSA), 0.02% Na azide in PBS) or gelatin (0.5%) for at least 30 min at RT.

Selection solutions (1 ml) contained biotinylated human HER2, phages, Na azide (0.02%), Tween 20 (0.05%) and either BSA (3%) or gelatin (0.1%) according to Table 2, and are prepared in PBS. The phages are incubated with biotinylated human HER2 target at 4° C. during three days for Cycle 4 and during one day for Cycle 5, followed by 1 h incubation under agitation at RT. The selection samples are transferred to blocked streptavidin beads for 15 min under agitation at RT. The beads are washed 10 times with 1 ml of selection buffer TPBSB (3%) (0.05% Tween20, 3% bovine serum albumin (BSA), 0.02% Na azide in PBS) or GT 0.1 (0.1% gelatin, 0.1% Tween 20 and 0.02% Na azide in PBS)), followed by 10 washes with PBS where the second last wash is performed for 5 min. Phages are either eluted with 1000 μl 50 mM glycine-HCl, pH 2.2, for 10 min at RT, followed by immediate neutralization with 900 μl PBS supplemented with 100 μl 1 M Tris-HCl, pH 8.0, or eluted with 1000 μl trypsin (2 mg/ml) for 30 min at RT followed by addition of 1000 μl aprotinin (0.4 mg/ml). The eluted phages (¾ of the volume) are used to infect 50 ml log phase *E. coli* RR1ΔM15 cells (Rüther, 1982, supra) after each cycle of selection. After 30 min incubation with gentle agitation and 30 min with vigorous agitation at 37° C., the cells are centrifuged and the pellet is dissolved in a smaller volume and spread on TYE plates (15 g/l agar, 10 g/l tryptone water (Merck), 5 g/l yeast extract, 3 g/l NaCl supplemented with 2% glucose and 100 μg/ml ampicillin) and finally incubated over night at 37° C.

Phage Stock Preparation

Cells from plates are re-suspended in TSB medium (30 g/l tryptic soy broth) and the cell concentration is determined by measuring the optical density at 600 nm assuming that $OD_{600}=1$ corresponds to $5 \times 10^8$ cells/ml. Cells are inoculated (approximately 100 times excess of cells compared to eluted phages) in 100 ml TSB+YE medium supplemented with 2% glucose and 100 μg/ml ampicillin and grown at 37° C. to approximately $OD_{600}=0.5$-0.7. Thereafter, 10 ml are transferred to a new flask and infected by 10 times molar excess of M13K07 helper phage (New England Biolabs, # NO315S) and incubated for 30 min with low agitation. Cells are pelleted at 2000 g for 10 min and resuspended in 100 ml TSB+YE medium supplemented with 100 µM isopropyl β-D-1-thiogalactopyranoside (IPTG), 50 µg/ml kanamycin and 100 µg/ml ampicillin and grown over night at 100 rpm and 25° C. A portion of the resuspended cells is stored at −80° C. as a glycerol stock.

The overnight culture is centrifuged at 2500 g for 10 min and phages in the supernatant are precipitated by adding ¼ of the volume of precipitation buffer (20% PEG/2.5 M NaCl) and incubated on ice for 1 hour. Precipitated phages are pelleted by centrifugation at 10000 g at 4° C. for 30 min, resuspended in 20 ml PBS and thereafter the precipitation procedure is repeated. The phages are finally resuspended in 1 ml PBS and filtered through a 0.45 µm filter.

Selection, wash and elution solutions are titrated after each round of selection. Phage solutions are diluted in sterile water in a microtiter plate and 100 µl log phase *E. coli* RR1ΔM15 cells are added to each phage dilution. After 20 min incubation at RT, 5 µl from each titration are transferred to a TYE plate and incubated over night at 37° C. The resulting colonies are counted and the titers (cfu/ml) calculated.

ELISA Analysis of HER2 Binding

Clones from the final selection cycles are expressed and screened for HER2 binding activity using an ELISA setup as described in Example 4 below (but using HER2 as target protein), or as described below. Randomly picked colonies are expressed in 96 deep-well plates by inoculating each colony into 1 ml TSB+YE medium supplemented with 100 µg/ml ampicillin and 1 mM IPTG and grown for 18-24 hours at 37° C. After incubation, replicate plates are made by transferring a small fraction of each culture to 96-well plates with 15% glycerol for storage at −20° C.

Remaining cells are pelleted by centrifugation at 3000 g for 10 min, re-suspended in 400 µl PBS-T 0.05 (PBS supplemented with 0.05% Tween 20) and frozen at −80° C. Frozen samples are thawed in a water bath and cells are pelleted at 3700 g for at least 20 min. Supernatants containing expressed molecules are collected and used in ELISA.

Half area microtiter wells (Costar, #3690) are coated over night at 4° C. with 50 µl of HSA at a concentration of 6 µg/ml in ELISA coating buffer (Sigma, #3041). The wells are blocked with 100 µl blocking buffer (2% non fat dry milk in PBS) for 2 h at RT. After removal of the blocking buffer, 50 µl of the prepared proteins are added to the wells, and plates are incubated for 1.5 h at RT. Supernatants are discarded, and biotinylated HER2 at a concentration of 0.5-10 µg/ml in PBS-T 0.05 is added to the wells and incubated for 1.5 h. Bound complexes are detected with horse radish peroxidase conjugated streptavidin (HRP, Dako, # P0397) diluted 1:5000 in PBS-T 0.05, incubated for 1 h at RT. 50 µl IMMUNOPURE TMB substrate (Pierce, #34021) are added to the wells and the plates are treated according to the manufacturer's recommendations. Absorbance of the wells is read at 450 nm in a Tecan Ultra 384 ELISA reader (Tecan) and evaluated using Magellan v. 5.0 software (Tecan). Prior to addition of each new reagent, four washes are done with PBS-T 0.05.

Based on the result of this experiment, clones are picked for sequencing as described next.

Sequencing of ELISA Positive Clones

PCR fragments from selected colonies are amplified using appropriate oligonucleotides. Sequencing of amplified fragments is performed using a BIGDYE Terminator v3.1 Cycle Sequencing Kit (Applied Biosystems) according to the manufacturer's recommendations and with the appropriate biotinylated oligonucleotide. The sequencing reactions are purified by binding to DYNABEADS REGEN streptavidin-coated paramagnetic beads using a Magnatrix 8000 instrument (Magnetic Biosolutions), and finally analyzed on ABI PRISM 3100 Genetic Analyser (Applied Biosystems).

Sub-Cloning into Plasmid pAY1448

DNA encoding selected and HER2-specific molecules is sub-cloned into the expression vector pAY1448 to create $His_6$-tagged monomeric molecules expressed as MGSSHH-HHHHLQ-[Z #####]-VD ($His_6$-Z #####) (SEQ ID No. 11), wherein Z ##### denotes an identified member of the starting population of variant molecules. Plasmids containing inserts are purified from 2 ml overnight cultures of *E. coli* RR1ΔM15 cells in TSB supplemented with 100 µg/ml ampicillin using Qiagen Mini Kit (Qiagen) according to manufacturer's recommendations.

DNA of selected molecules is sub-cloned into the expression vector pAY1448 by Accl-Notl PCR sticky end cloning using the appropriate PCR primer pairs.

The expression vector pAY1448 is digested in two steps at 37° C. for 4 h using Accl and Notl in NEB4 and NEB3 buffer (New England Biolabs), respectively, and dephosphorylated with calf intestinal alkaline phosphatase (CIAP; Fermentas) for 1 h at 37° C. The cleaved plasmid and fragments are purified by QIAquick PCR purification kit (Qiagen) according to the manufacturer's recommendations.

The PCR products are hybridized and ligated into Accl-Notl digested and dephosphorylated pAY1448 for 1 h at RT using T4 DNA ligase (5 units/µl; Fermentas). Aliquots of the ligations are electroporated into *E. coli* BL21(DE3) cells. The cells are plated on tryptose blood agar base (TBAB) plates supplemented with 50 µg/ml kanamycin and incubated over night at 37° C. Positive clones are first verified for inserts with PCR screening and then analyzed for correct sequences as described above.

Expression and Purification of $His_6$-Tagged Polypeptides

Selected molecules, all sub-cloned into pAY1448 as described above, are expressed in *E. coli* BL21(DE3) as fusions to an N-terminal $His_6$-tag and purified by IMAC. A colony of each molecule is used to inoculate 5 ml TSB medium supplemented with 50 µg/ml kanamycin. The cultures are grown over night at 37° C. The following day, 50 µl of each culture are inoculated separately to 100 ml TSB+YE medium supplemented with 50 µg/ml kanamycin in a 1 liter flask. The cultures are grown at 100 rpm at 37° C. to an $OD_{600}$ of 0.7-1, after which IPTG is added to a final concentration of 0.5 mM and cells are incubated at RT over night at 100 rpm. Cultures are harvested by centrifugation at 8000 g for 5 minutes and pellets are stored in a freezer until protein preparation.

The $His_6$-tagged proteins are IMAC purified under denatured conditions using 1.5 ml Ni-NTA Superflow columns (Qiagen). The buffer is exchanged to PBS using PD-10 columns (GE Healthcare).

Protein concentration is determined using $A_{280}$ and the BCA Protein Assay Reagent Kit (Pierce) as recommended by the manufacturer. The purity of the proteins is analyzed by SDS-PAGE stained with Coomassie Blue R.

Biosensor Analysis of Selected Molecules' Affinity for Human HER2

Biosensor analysis on a BIACORE 2000 instrument (GE Healthcare) is performed with human HER2 immobilized by amine coupling onto the carboxylated dextran layer on the surface of a CM-5 chip (research grade; GE Healthcare) according to the manufacturer's recommendations. Surface 1 on the chip is activated and deactivated and used as reference cell during injections. The selected molecules, expressed and purified as described above, are diluted in HBS-EP (GE Healthcare) to 25 nM and injected at a constant flow-rate of 25 µl/min for 10 minutes, followed by dissociation in HBS-EP for 30 minutes. The surfaces are regenerated with two injections of 25 mM HCl.

Example 3—Cloning, Production and Evaluation of Melting Temperature and In Vitro Antigenicity of Original and Inventive Scaffold Variants Summary This example describes the cloning, production and evaluation of original and inventive scaffold variants. The introduced scaffold mutations are believed to improve several properties of the polypeptide molecules, such as antigenicity, hydrophilicity and alkaline and structural stability. Thus, different molecules were evaluated for melting temperature and in vitro antigenicity and the results showed that inventive molecules had increased melting temperatures and displayed lower in vitro antigenicities (lower IgG binding) as compared to original molecules.

Cloning of Polypeptides

For original constructs, DNA sequences encoding molecules specific for Tumor Necrosis Factor-alpha (TNF-α), HER2, insulin, Taq polymerase and Platelet Derived Growth Factor-Receptor beta (PDGF-Rβ) (Table 3) were amplified by PCR in two individual reactions each (PCR1 and PCR2). Primer pairs AFFI-267/AFFI-1014 and AFFI-1015/AFFI-270 (Table 4), encoding parts of the Accl restriction site in the 5'-ends, were applied in PCR1 and PCR2 respectively. To prepare the plasmid templates, bacteria harboring the plasmid DNA were grown overnight in TSB medium, supplemented with 50 μg/ml of kanamycin. The cells were pelleted by centrifugation and plasmids were prepared using QIAprep Spin Miniprep Kit (Qiagen).

For inventive constructs, PCR amplification (PCR1 and PCR2) of nucleotide sequences encoding modified, inventive molecules was performed using partially overlapping oligonucleotides as templates (AFFI-1320-AFFI-1323, AFFI-1326 and AFFI-1327) or using vector with original construct and oligonucleotides containing relevant mutations (AFFI-69, AFFI-70, AFFI-1151 and AFFI-1152) (Table 4). Primer pairs AFFI-1328/AFFI-1331 and AFFI-1329/AFFI-1330, encoding parts of the Accl restriction site in the 5'-ends, were included in the PCR reactions.

The PCR reactions were amplified using Pfu Turbo DNA polymerase (Stratagene, #600854-52) according to a standard PCR protocol and the PCR products were analyzed by 1% agarose gel electrophoresis.

The PDGF-Rβ binding Z variants were generated using oligonucleotides with varied codons and a PCR based mutagenesis technique. Obtained PCR fragments were ligated into a cleaved expression vector using In-Fusion technology (Clontech, #639607).

To generate DNA fragments containing upstream and downstream Accl sticky-ends for all constructs, forward and reverse nucleotide strands of the PCR1 and PCR2 products were separated using magnetic streptavidin beads. After 30 min incubation at RT under continuous rotation, the beads were washed with wash buffer (50 mM Tris-HCl pH 7.5, 10 mM $MgCl_2$, 10 mM DTT) and heated to 95° C. for 5 min. The supernatant containing the non-biotinylated fragments was collected and heated to 95° C., followed by stepwise cooling to 25° C. during 30 min to hybridize the DNA strands.

The DNA fragments encoding binding molecules were subsequently ligated at RT, either for 2 h or overnight, into a CIP-treated (calf intestinal alkaline phosphate) and purified expression vector, previously digested with Accl restriction enzyme. The achieved constructs were MGSSHHHHHHLQ-[Z #####]-VD (SEQ ID No. 11), MGSSLQ-[Z #####]-VDC (for $Z_{PDGF-R\beta:2465}$) (SEQ ID No. 12) or M-[Z #####]-C (for $Z_{PDGF-R\beta:3358}$).

The ligations were transformed into electrocompetent *E. coli* TOP10 cells and cultivated on plates as described in Example 2. Bacterial colonies harboring the newly constructed plasmids were PCR screened, and the insert DNA sequences were verified as described in Example 2.

Verified plasmids were prepared as described earlier.

Expression of Polypeptides

*E. coli* BL21(DE3) cultures transformed with relevant plasmids were inoculated into 800 ml TSB-YE medium supplemented with 50 μg/ml kanamycin and 0.3 ml/l antifoam agent (Breox FMT 30) and grown at 37° C. to an OD600 of approximately 2. Protein expression was then induced by addition of 1 M IPTG to a final concentration of 0.5 mM. The cultivations were performed using the multifermenter system Greta (Belach). The cultures were harvested 5 h after induction by centrifugation at 15 900×g for 20 min. Supernatants were discarded and the cell pellets collected and stored at −20° C. The protein expression level was determined using SDS-PAGE and ocular inspection of stained gels.

Purification of Expressed Polypeptides

Proteins with $His_6$ tag were purified as follows: Pelleted bacterial cells harboring soluble $His_6$ tagged polypeptides were suspended in His GRAVITRAP binding buffer (20 mM sodium phosphate, 0.5 M NaCl, 20 mM imidazole and 40 U/ml BENZONASE) and disrupted by ultrasonication. After clarification, the supernatants were loaded on His GRAVITRAP columns (GE Healthcare) previously equilibrated with His GRAVITRAP binding buffer. After washing the columns with 10 column volumes (CV) of His GRAVITRAP washing buffer (20 mM sodium phosphate, 0.5 M NaCl, 60 mM imidazole), the polypeptides were eluted with 3 CV His GRAVITRAP elution buffer (20 mM sodium phosphate, 0.5 M NaCl, 500 mM imidazole).

Proteins without $His_6$ tag were purified as follows: Pelleted bacterial cells harboring soluble $Z_{PDGF-R\beta:2465}$-Cys or $Z_{PDGF-R\beta:3358}$-Cys were suspended in 20 mM Tris-HCl, pH 7.1. To disrupt the cells and release the intracellular content, the cell suspensions were heated to 85° C. for 3 minutes. The lysates were clarified by centrifugation followed by filtration, and loaded on 25 ml Q Sepharose FF (GE Healthcare) packed in an XK26 column (GE Healthcare), previously equilibrated with 20 mM Tris-HCl, pH 7.1. After column wash with 5 CV 20 mM Tris-HCl, pH 7.1, bound proteins were eluted with a linear gradient of 0-0.5 M NaCl in 20 mM Tris-HCl, pH 7.1, during 10 CV. The flow rate was 5 ml/min and the 280 nm signal was monitored. Fractions containing $Z_{PDGF-R\beta:\ 2465}$-CYS or $Z_{PDGF-R\beta:3358}$-Cys were identified by SDS-PAGE analysis. Relevant fractions were pooled and pH was adjusted to 8.0 by addition of 1 M Tris-HCl, pH 8.0, to a final concentration of 50 mM. The C-terminal cysteine on the constructs was reduced by addition of DTT to 20 mM, followed by incubation at 40° C. for 3 minutes. After reduction, acetonitrile (ACN) was added to a final concentration of 5% and reduced $Z_{PDGF-R\beta:2465}$-Cys or $Z_{PDGF-R\beta:\ 3358}$-Cys was loaded on 1 ml Resource 15 RPC columns (GE Healthcare), previously equilibrated with RPC A Buffer (0.1% TFA, 5% ACN, 95% water). After column wash with 10 CV RPC A Buffer, bound proteins were eluted with a linear gradient of 0-40% RPC B Buffer (0.1% TFA, 80% ACN, 20% water). The flow rate was 1 ml/min and the 280 nm signal was monitored. Fractions containing pure $Z_{PDGF-R\beta:2465}$-Cys or $Z_{PDGF-R\beta:3358}$-Cys were identified by SDS-PAGE analysis and pooled.

To enable lyophilization of the proteins, the buffer was exchanged to either 10 mM ammonium hydrogen carbonate buffer, pH 8.0, or 10 mM ammonium acetate buffer, pH 6.0, using disposable PD-10 desalting columns (GE Healthcare). The lyophilization buffer was chosen in regard to the isoelectric point of relevant proteins. Finally, the binding polypeptides $His_6$-$Z_{TNF-\alpha:185}$, $His_6$-$Z_{HER2:342}$, $His_6$-$Z_{Insulin:810}$, $His_6$-$Z_{Taq:1154}$, $Z_{PDGF-R\beta:2465}$-Cys, $His_6$-$Z_{HER2:2628}$, $His_6$-$Z_{Taq:3229}$, $His_6$-$Z_{TNF-\alpha:3230}$, $His_6$-$Z_{Insulin:3232}$ and $Z_{PDGF-R\beta:3358}$-Cys were lyophilized using a Christ Alpha 2-4 LSC instrument and stored at 4° C. until use (Table 5). The free C-terminal cysteine was blocked using N-ethylmalemide (NEM) according to the manufacturer's recommendations (Pierce).

Analysis of Purified Polypeptides

Determination of the concentration of polypeptide solutions was performed by measuring the absorbance at 280 nm using a NANODROP ND-1000 Spectrophotometer. The proteins were further analyzed with SDS-PAGE and LC-MS.

For the SDS-PAGE analysis, approximately 10 μg polypeptide was mixed with LDS Sample Buffer and DTT (45 mM final concentration), incubated at 70° C. for 15 min and loaded onto NUPAGE 4-12% Bis-Tris Gels. The gels were run with MES SDS Running Buffer in a Novex Mini-Cell employing the SEEBLUE Plus2 Prestained Standard as molecular weight marker and PAGEBLUE Protein Staining Solution for staining.

To verify the identity of the polypeptides, LC/MS analyses were performed using an Agilent 1100 LC/MSD system, equipped with API-ESI and a single quadruple mass analyzer. After buffer exchange, protein samples were diluted in lyophilization buffer to a final concentration of 0.5 mg/ml and 10 μl were loaded on a Zorbax 300SB-C8 Narrow-Bore column (2.1×150 mm, 3.5 μm) at a flow-rate of 0.5 ml/min. Proteins were eluted using a linear gradient of 10-70% solution B for 30 min at 0.5 ml/min. The separation was performed at 30° C. The ion signal and the absorbance at 280 and 220 nm were monitored. The molecular weights of the purified proteins were determined by analysis of the ion signal.

Determination of Melting Temperature (Tm)

Lyophilized polypeptides were dissolved in PBS to a final concentration of approximately 0.5 mg/ml and stored on ice. CD analysis was performed on a Jasco J-810 spectropolarimeter in a cell with an optical path-length of 1 mm. In variable temperature measurements, the absorbance was measured at 221 nm from 20 to 80° C., with a temperature slope of 5° C./min. Melting temperatures (Tm) for the tested polypeptides were calculated by determining the midpoint of the transition in the CD vs temperature plot.

The polypeptide molecules modified in accordance with the invention had increased melting temperatures as compared to the original molecules (Table 6). In FIG. 1, the obtained melting curve for $His_6$-$Z_{TNF-\alpha:3230}$ (inventive TNF-α specific polypeptide) is shown.

In Vitro Antigenicity ELISA (Analysis of IgG Binding in Serum)

The general conditions for the ELISA were as follows: the ELISA assays were performed in half area, 96-well plates. Volumes used were 50 μl per well for all incubations except for blocking where 100 μl was used. Coating was done over night at 4° C. in coating buffer (15 mM $Na_2CO_3$ and 35 mM $NaHCO_3$), and all other incubations were performed at room temperature. Dilution of primate serum and detection antibodies was made in PBS+0.5% casein. All washes were done using an automatic ELISA Scan Washer 300, where each well was washed four times with 175 μl washing buffer (PBS-T; 0.05% Tween 20 in 1×PBS) per wash.

The wells of the ELISA plate were coated with 2 μg/ml of the binding polypeptides $His_6$-$Z_{TNF-\alpha:185}$, $His_6$-$Z_{HER2:342}$, $His_6$-$Z_{Insulin:810}$, $His_6$-$Z_{Taq:1154}$, $Z_{PDGF-R\beta:\ 2465}$-Cys-NEM, $His_6$-$Z_{HER2:2628}$, $His_6$-$Z_{Taq:3229}$, $His_6$-$Z_{TNF-\alpha:3230}$, $His_6$-$Z_{Insulin:3232}$ and $Z_{PDGF-R\beta:3358}$-Cys-NEM. $Z_{HER2:342}$ was used as standard. After coating, the wells were washed twice with tap water and blocked with PBS+0.5% casein. The plate was emptied and a 2-fold dilution series of a primate serum pool from cynomolgus monkey (MAccaca fascicularis; obtained from Swedish Institute for Infectious Disease Control) was added to the wells. The titration series started with a 1/100 dilution and ended at 1/102400. The dilution was done directly in the 96-well plate. After incubating one hour with the primate serum pool, the plate was washed and a goat anti-human Ig-HRP antibody was added in dilution 1/5000 for detection. After 50 minutes incubation with the detection antibody, the plate was washed and the substrate added. Equal volumes of the two components in the IMMUNOPURE TMB kit were mixed, and 50 μl was added per well. Subsequently, the plate was incubated in the dark for 12 minutes, and the reaction was stopped by addition of 50 μl stop solution (2 M $H_2SO_4$). The absorbance at 450 nm was recorded using an ELISA reader. As negative control, PBS+0.5% casein was used instead of the primate serum pool.

To evaluate the results and to obtain an IVA value that represents the level of primate Ig-molecules binding to the polypeptide, the program GraphPad Prism 5 was used. Sample values, with background OD values subtracted, were added to a template based on a XY-non-linear regression (sigmoidal dose response) formula. A dilution value for OD 0.3 was obtained from the formula and the IVA values were calculated by setting standard dilution value to 100 and by relating all samples to 100. A value below 100 indicates a decreased ability of the tested polypeptide to bind to immunoglobulins as compared to the $Z_{HER2:342}$ molecule used as a positive control.

The inventive molecules showed less potential to bind immunoglobulins as compared with original molecules (Table 7). The results are shown as in vitro antigenicity (IVA) values, and a reduced in vitro antigenicity (IgG binding) is read as a decrease in the IVA value.

TABLE 3

List of binding polypeptide sequences

| Name | Amino acid sequence |
|---|---|
| $Z_{TNF-\alpha:185}$ | VDNKFNKELGWAIGEIGTLPNLNHQQFRAFILSLWDD PSQSANLLAEAKKLNDAQAPK (SEQ ID No. 13) |
| $Z_{HER2:342}$ | VDNKFNKEMRNAYWEIALLPNLNNQQKRAFIRSLYDD PSQSANLLAEAKKLNDAQAPK (SEQ ID No. 14) |
| $Z_{Insulin:810}$ | VDNKFNKEKYMAYGEIRLLPNLNHQQVMAFIDSLVD DPSQSANLLAEAKKLNDAQAPK (SEQ ID No. 15) |
| $Z_{Taq:1154}$ | VDNKFNKEKGEAVVEIFRLPNLNGRQVKAFIASLYDD PSQSANLLAEAKKLNDAQAPK (SEQ ID No. 16) |
| $Z_{PDGF-R\beta:2465}$ | VDNKFNKELIEAAAEIDALPNLNRRQWNAFIKSLVD DPSQSANLLAEAKKLNDAQAPK (SEQ ID No. 17) |

TABLE 4

List of oligonucleotides

| Name | Sequence 5'-3' |
|---|---|
| AFFI-069 | GTGAGCGGATAACAATTCCCCTC (SEQ ID No. 18) |
| AFFI-070 | CAGCAAAAAACCCCTCAAGACCC (SEQ ID No. 19) |
| AFFI-115 | CAGCAAAAAACCCCTCAAGACCC (SEQ ID No. 20) |
| AFFI-267 | AGATAACAAATTCAACAAAG (SEQ ID No. 21) |
| AFFI-270 | CTACTTTCGGCGCCTGAGCATCATTTAG (SEQ ID No. 22) |
| AFFI-1014 | ACTTTCGGCGCCTGAGCATCATTTAG (SEQ ID No. 23) |
| AFFI-1015 | ATAACAAATTCAACAAAGAA (SEQ ID No. 24) |
| AFFI-1043 | ACTTTCGGCGCCTGAGAATCATTTAGCTTTTA (SEQ ID No. 25) |
| AFFI-1044 | CTACTTTCGGCGCCTGAGAATCATTTAGCTTTTA (SEQ ID No. 26) |
| AFFI-1143 | AGATGCCAAATACGCCAAAGAAATGCGAA (SEQ ID No. 27) |
| AFFI-1144 | ATGCCAAATACGCCAAAGAAATGCGAA (SEQ ID No. 28) |
| AFFI-1151 | CCCAAGCCAAAGCTCTGAATTGCTATCAGAAGCTAAAAGC (SEQ ID No. 29) |
| AFFI-1152 | GCTTTTTAGCTTCTGATAGCAATTCAGAGCTTTGGCTTGGG (SEQ ID No. 30) |
| AFFI-1320 | AGATGCCAAATACGCCAAAGAAAAGGGGGAGGCGGTGGTT GAGATCTTTAGGTTACCTAACTTAACCGGGAGGCAAGTGAA GGCCTTCATCGCGAAATTATA (SEQ ID No. 31) |
| AFFI-1323 | CTACTTTCGGCGCCTGGCTATCATTTAGCTTTTTAGCTTCG CTCAGTAATTCAGAGCTCTGGCTTGGGTCATCCCATAATTT AAGGATGAAGGCCCGAAATT (SEQ ID No. 32) |
| AFFI-1326 | AGATGCCAAATACGCCAAAGAAAAGTATATGGCGTATGGTG AGATCCGGTTGTTACCTAACTTAACCCATCAGCAAGTTATG GCCTTCATCGATAAATTAGT (SEQ ID No. 33) |
| AFFI-1327 | CTACTTTCGGCGCCTGGCTATCATTTAGCTTTTTAGCTTCG CTCAGTAATTCAGAGCTCTGGCTTGGGTCATCCACTAATTT ATCGATGAAGGCCATAACTT (SEQ ID No. 34) |
| AFFI-1328 | AGATGCCAAATACGCCAAAG (SEQ ID No. 35) |
| AFFI-1329 | ATGCCAAATACGCCAAAGAA (SEQ ID No. 36) |
| AFFI-1330 | CTACTTTCGGCGCCTGGCTATCATTTAG (SEQ ID No. 37) |
| AFFI-1331 | ACTTTCGGCGCCTGGCTATCATTTAG (SEQ ID No. 38) |

TABLE 5

List of tested polypeptides

| Target | Designation | Variant |
|---|---|---|
| TNF-alpha | $His_6$-$Z_{TNF-\alpha:185}$ | Original |
| TNF-alpha | $His_6$-$Z_{TNF-\alpha:3230}$ | Inventive |
| HER2 | $Z_{HER2:342}$ | Original |
| HER2 | $His_6$-$Z_{HER2:342}$ | Original |
| HER2 | $His_6$-$Z_{HER2:2628}$ | Inventive |
| Insulin | $His_6$-$Z_{Insulin:810}$ | Original |
| Insulin | $His_6$-$Z_{Insulin:3232}$ | Inventive |
| Taq polymerase | $His_6$-$Z_{Taq:1154}$ | Original |
| Taq polymerase | $His_6$-$Z_{Taq:3229}$ | Inventive |
| PDGF-Rβ | $Z_{PDGF-R\beta:2465}$-Cys | Original |
| PDGF-Rβ | $Z_{PDGF-R\beta:3558}$-Cys | Inventive |

TABLE 6

Determined Tm values of tested polypeptides

| Target | Designation | Variant | Tm (° C.) |
|---|---|---|---|
| TNF-alpha | $His_6$-$Z_{TNF-\alpha:185}$ | Original | 53 |
| TNF-alpha | $His_6$-$Z_{TNF-\alpha:3230}$ | Inventive | 60 |
| HER2 | $His_6$-$Z_{HER2:342}$ | Original | 63 |
| HER2 | $His_6$-$Z_{HER2:2628}$ | Inventive | 69 |
| Insulin | $His_6$-$Z_{Insulin:810}$ | Original | 42 |
| Insulin | $His_6$-$Z_{Insulin:3232}$ | Inventive | 48 |
| Taq polymerase | $His_6$-$Z_{Taq:1154}$ | Original | 46 |
| Taq polymerase | $His_6$-$Z_{Taq:3229}$ | Inventive | 50 |
| PDGF-Rβ | $Z_{PDGF-R\beta:2465}$-Cys-NEM | Original | 42 |
| PDGF-Rβ | $Z_{PDGF-R\beta:3558}$-Cys-NEM | Inventive | 42 |

TABLE 7

IVA values of tested polypeptides

| Target | Designation | Variant | IVA-value |
|---|---|---|---|
| TNF-alpha | $His_6$-$Z_{TNF-\alpha:185}$ | Original | 38 |
| TNF-alpha | $His_6$-$Z_{TNF-\alpha:3230}$ | Inventive | 21 |
| HER2 | $His_6$-$Z_{HER2:342}$ | Original | 99 |
| HER2 | $His_6$-$Z_{HER2:2628}$ | Inventive | 14 |
| Insulin | $His_6$-$Z_{Insulin:810}$ | Original | 43 |
| Insulin | $His_6$-$Z_{Insulin:3232}$ | Inventive | 16 |
| Taq polymerase | $His_6$-$Z_{Taq:1154}$ | Original | 26 |
| Taq polymerase | $His_6$-$Z_{Taq:3229}$ | Inventive | 18 |
| PDGF-Rβ | $Z_{PDGF-R\beta:2465}$-Cys-NEM | Original | 35 |
| PDGF-Rβ | $Z_{PDGF-R\beta:3558}$-Cys-NEM | Inventive | 3 |

Example 4—Phage Display Selection and Characterization of Dynazyme Binding Polypeptide Variants Biotinylation of Dynazyme The target protein Dynazyme II DNA polymerase (Dynazyme) from species *Thermus brockianus* (Finnzymes, # F-501 L) was biotinylated using a 10× molar excess of NO-WEIGHT Sulfo-NHS-LC-biotin (Pierce, #21327) according to the manufacturer's protocol. Buffer was changed by dialysis using Slide-a-lyzer dialysis cassette (Pierce, 10K, 0.5-3 ml) to PBS prior to biotinylation and to TKMT (10 mM Tris-HCl, 50 mM KCl, 1.5 mM $MgCl_2$, 0.1% Triton X-100, pH 8.8) after biotinylation to remove unbound biotin.

Phage Display Selection

Selection was performed against biotinylated Dynazyme using the inventive population of polypeptides (Example 1). Two approaches for selection were utilized; one with a high target concentration (track 1) and one with a low target concentration (track 2). Four selection cycles were performed. New phage stocks were prepared between each cycle. For selection overview and details, see FIG. 2.

Phage library stock was PEG/NaCl precipitated twice as described in Example 2 and dissolved in TKMT supplemented with 0.1% gelatin (TKMTg). Phages were pre-incubated with streptavidin-coated beads (SA beads, DYNABEADS M-280) for 30 minutes at RT. Beads used in the selection procedure and all tubes were pre-blocked in TKMTg.

Figure 2:
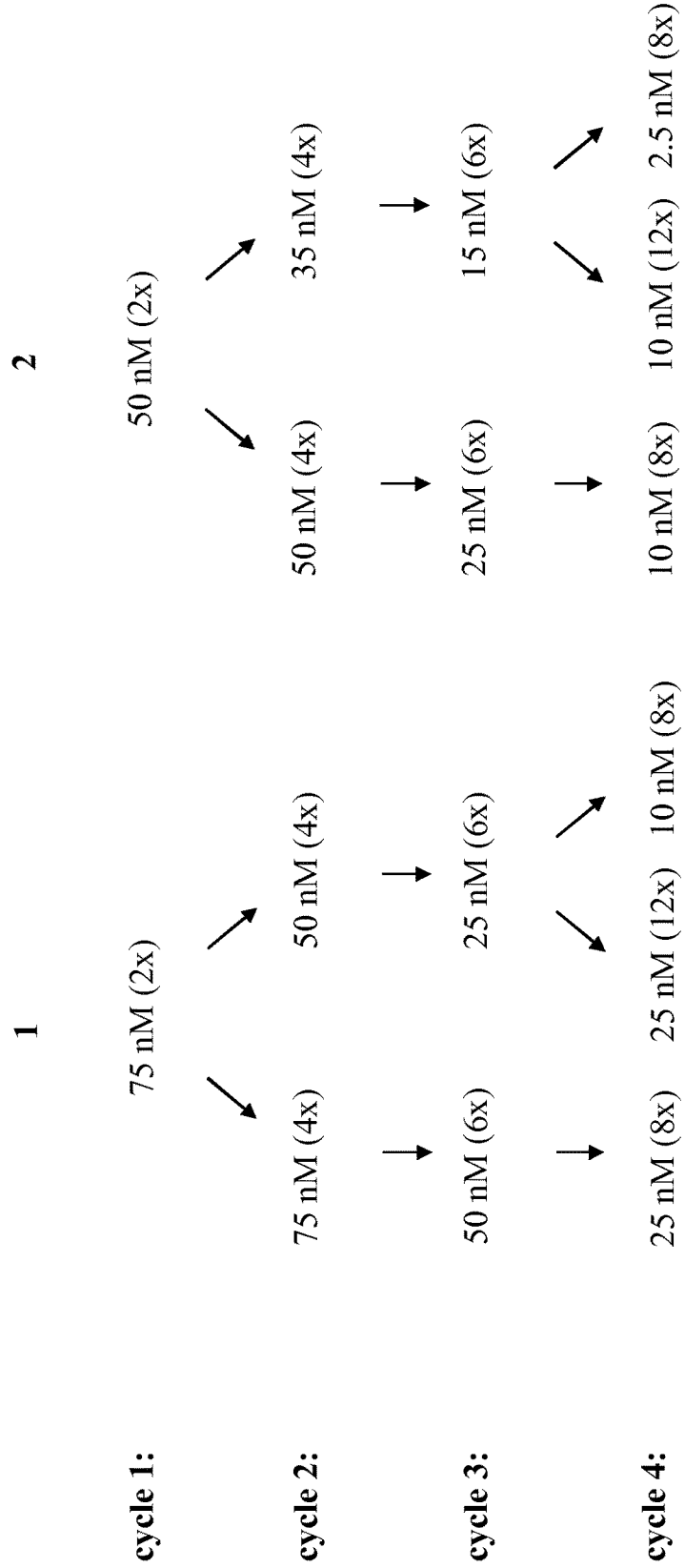
FIG. 2 shows an overview of the selection described in Example 4. Selection was performed in two different tracks, one with a high target concentration (track 1) and one with a low target concentration (track 2). Target concentrations are given for each track and cycle as well as the number of washes (within parentheses).

The target concentrations and the number of washes in each cycle are presented in FIG. 2. Buffer used for selection and washes was TKMTg. Pre-selected phages were incubated with the biotinylated target for 17 hours at 4° C. followed by 3 hours at RT during the first cycle and 3 hours or 1 hour, respectively, during the following cycles. Subsequently, the phage particles were transferred to pre-blocked SA beads, 5 mg (first cycle track 1), 3.5 mg (first cycle track 2) or 0.5 mg (all other cycles), and incubated for 10 min with agitation. Thereafter, the beads were washed and phage particles were eluted with a low pH buffer as described in Example 2. The eluted phages were used to infect log phase E. coli RR1ΔM15 cells after each round of selection. After 20 min incubation at 37° C., the cells were harvested by centrifugation. The pellet was dissolved in a small volume of TSB-YE, spread onto TYE plates and incubated overnight at 37° C. Phage stocks were prepared between each cycle essentially as described in Example 2. The phage particle titers and yields were calculated after each selection cycle. The phage particle yield (phage particles out/phage particles in) increased for each cycle (except the second one), indicating an enrichment in target binding clones.

ELISA Analysis of Dynazyme Binding Polypeptides

Clones obtained after the last round of selection were randomly picked and used for periplasmic protein expression in a 96-well plate format as described in Example 2. Supernatants containing soluble polypeptide variants fused to ABD were assayed for target binding in an ELISA as follows. The putative binding polypeptides were expressed as AQLE-[Z #####]-VDYV-[ABD]-SQKA (SEQ ID NO. 39) (ABD=the albumin binding domain GA3 from Streptococcus sp. G148, Kraulis et al (1996) FEBS Lett. 378(2): 190-194), wherein Z ##### denotes individual variants of the inventive polypeptide population.

Half area microtiter wells (Costar, #3690) were coated with 50 μl of 2-3 μg/ml Dynazyme in ELISA coating buffer. The wells were blocked with 100 μl TKMT complemented with 0.5% casein (Sigma) (TKMT-casein) for 1 h at RT. After removal of blocking solution, 50 μl of supernatants were added to the wells and the plates were incubated for 1.5 h at RT. Captured polypeptide variants were detected by adding a primary and then a secondary antibody. The primary antibody, an affinity purified polyclonal rabbit Ig against Z variants, was diluted 1:5000 in TKMT-casein and incubated for 1.5 h at RT. The secondary antibody, a goat α-rabbit-HRP Ig (DakoCytomation, # PO448), was diluted 1:5000 in TKMT-casein and incubated for 1 h at RT. The plates were washed four times with TKMT before incubation with the antibodies and the developing solution.

Plates were developed as described in Example 2 and read at 450 nm in an ELISA spectrophotometer. All plates were prepared with relevant negative and positive controls as well as a blank where TKMT was used instead of periplasmic supernatant. In total, 1080 randomly picked clones were screened in ELISA for their binding to Dynazyme. Positive clones and some clones with low absorbance values were selected for sequencing.

Sequencing of ELISA Positive Polypeptides

Individual clones were subjected to sequencing according to Example 2. Eleven unique binding polypeptides regarded as positive in ELISA screening were found. Some of the clones occurred in several copies. In addition, several sequences from clones with lower ELISA values were identified.

Sub-Cloning of Polypeptides into Plasmid pAY1448

Fifteen unique polypeptides were subjected to subcloning as monomers into the expression vector pAY1448 providing an N-terminal $His_6$-tag (as described in Example 2) using prepared plasmids as templates for the sticky-end PCR. The subcloning was performed as described in Example 3.

Purification of Polypeptides

The following text describes the purification of fifteen monomeric $His_6$-tagged polypeptides, namely $His_6$-Z04665, $His_6$-Z04672, $His_6$-Z04674, $His_6$-Z04678, $His_6$-Z04687, $His_6$-Z04767, $His_6$-Z04770, $His_6$-Z04775, $His_6$-Z04776, $His_6$-Z04777, $His_6$-Z04778, $His_6$-Z04779, $His_6$-Z04780, $His_6$-Z04781 and $His_6$-Z04899. Pelleted bacterial cells harboring the soluble $His_6$-tagged molecules were suspended in His GRAVITRAP binding buffer (20 mM sodium phosphate, 0.5 M NaCl, 20 mM imidazole and 25 U/ml BENZONASE) and disrupted by ultrasonication. The sonicated cell suspensions were heated using hot water (95° C.) until the temperature of the suspensions stabilized at around 90° C. during five minutes. After clarification by centrifugation, the supernatants were loaded on His GRAVITRAP columns (GE Healthcare) previously equilibrated with His GRAVITRAP binding buffer. After washing the columns with 5 CV His GRAVITRAP binding buffer and 5 CV His GRAVITRAP washing buffer (20 mM sodium phosphate, 0.5 M NaCl, 60 mM imidazole), the polypeptides were eluted with 3 CV His GRAVITRAP elution buffer (20 mM sodium phosphate, 0.5 M NaCl, 500 mM imidazole).

The polypeptide variants were further purified by reversed phase chromatography (RPC). Acetonitrile (ACN) was added to a final concentration of 2% in the eluted fractions from His GRAVITRAP. Samples were loaded on a RESOURCE RPC 3 ml column (GE Healthcare), previously equilibrated with RPC A buffer (0.1% trifluoroacetic acid (TFA), 2% ACN, 98% water). After column wash with 5 CV RPC A buffer, bound protein were eluted with a 20 CV linear gradient of 0-50% RPC B buffer (0.1% TFA, 80% ACN, 20% water). The flow rate was 5 ml/min and the 280 nm signal was monitored. Fractions containing pure polypeptides were identified by SDS-PAGE analysis and pooled.

The buffer of the purified polypeptides was replaced to 50 mM Tris-HCl, pH 8.8, by size exclusion chromatography on disposable PD-10 Desalting Columns (GE Healthcare).

Twelve of the fifteen polypeptide variants were successfully purified: $His_6$-Z04665, $His_6$-Z04672, $His_6$-Z04674, $His_6$-Z04687, $His_6$-Z04770, $His_6$-Z04775, $His_6$-Z04776, $His_6$-Z04777, $His_6$-Z04778, $His_6$-Z04780, $His_6$-Z04781 and $His_6$-Z04899.

Analysis of Purified Polypeptides

Determination of the concentration of polypeptide solutions was performed by measuring the absorbance at 280 nm using a NANODROP ND-1000 Spectrophotometer. The proteins were further analyzed with SDS-PAGE and LC-MS.

For the SDS-PAGE analysis, polypeptide solution was mixed with LDS Sample Buffer (Invitrogen) and incubated at 74° C. for 10 min. 10 μg of each polypeptide variant were loaded on NUPAGE 4-12% Bis-Tris Gels (Invitrogen). The gels were run with MES SDS Running Buffer (Invitrogen) in an XCELL SURELOCK Mini-Cell (Invitrogen) employing NOVEX Sharp Prestained Protein Standard (Invitrogen) as molecular weight marker and PhastGel™ Blue R (GE Healthcare) protein staining solution for staining.

To verify the identity of the polypeptide variants, LC/MS-analyses were performed using an Agilent 1100 LC/MSD system equipped with API-ESI and single quadruple mass analyzer. The protein samples were diluted in 50 mM Tris-HCl, pH 8.8, to a final concentration of 0.5 mg/ml and 10 µl were loaded on a Zorbax 300SB-C18 column (4.6× 150, 3.5 µm) (Agilent) at a flow-rate of 1 ml/min. Solution A contained 0.1% TFA in water and solution B contained 0.1% TFA in ACN. Proteins were eluted using a 22 minutes linear gradient of 15% to 65% solution B at 1 ml/min. The separation was performed at 30° C. The ion signal and the absorbance at 280 and 220 nm were monitored. The molecular weights of the purified proteins were verified by analysis of the ion signal.

Purity of the polypeptide variants was determined to be greater than 95% according to the SDS-PAGE and LC/MS-analyses.

Determination of Melting Temperature (Tm)

Purified polypeptide variants were diluted in 50 mM Tris-HCl, pH 8.8, to a final concentration of 0.5 mg/ml. Circular dichroism (CD) analysis was performed on a Jasco J-810 spectropolarimeter in a cell with an optical path-length of 1 mm. In the variable temperature measurements, the absorbance was measured at 221 nm from 20° to 90° C., with a temperature slope of 5° C./min. Polypeptide melting temperatures (Tm) were calculated by determining the midpoint of the transition in the CD vs. temperature plot. For results, see Table 8.

TABLE 8

Tm of Dynazyme binding polypeptide variants

| Designation | Tm (° C.) |
|---|---|
| $His_6$-Z04665 | 38 |
| $His_6$-Z04672 | 33 |
| $His_6$-Z04674 | 35 |
| $His_6$-Z04687 | 60 |
| $His_6$-Z04770 | 44 |
| $His_6$-Z04775 | 45 |
| $His_6$-Z04776 | 55 |
| $His_6$-Z04777 | 58 |
| $His_6$-Z04778 | 43 |
| $His_6$-Z04780 | 65 |
| $His_6$-Z04781 | 66 |
| $His_6$-Z04899 | 39 |

Analysis of Heat Stability

Figure 3:
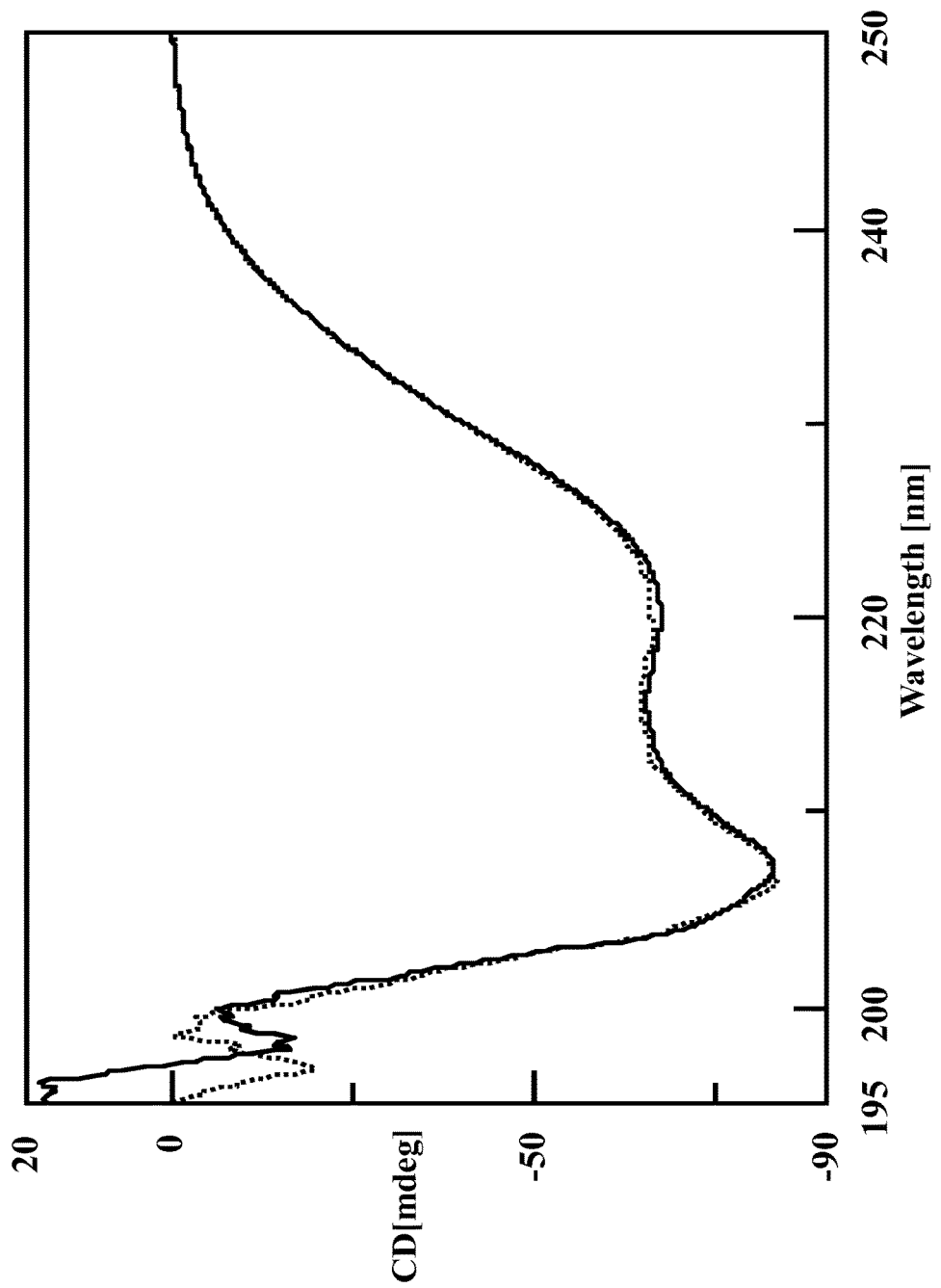
FIG. 3 is an overlay plot of two CD spectra before (full line) and after (dashed line) heating of $His_6$-Z04674 to 96° C.

The ability to refold to the original alpha helical structure after being subjected to heat was a requested property of the above described polypeptide variants. To investigate structural reversibility, two CD spectra per sample were obtained at 20° C. Between the two measurements, the samples were heated to 96° C. The samples were kept at 96° C. for two minutes, and then cooled to 20° C. Similar CD spectra before and after heating would prove a sample to be structurally reversible. Three of twelve analyzed polypeptide variants were negatively affected by the heat treatment, whereas nine polypeptide variants were shown to regain their alpha helical structure completely. A typical overlay of two CD spectra before and after heating is shown in FIG. 3.

BIACORE Binding Analysis

Figure 4:
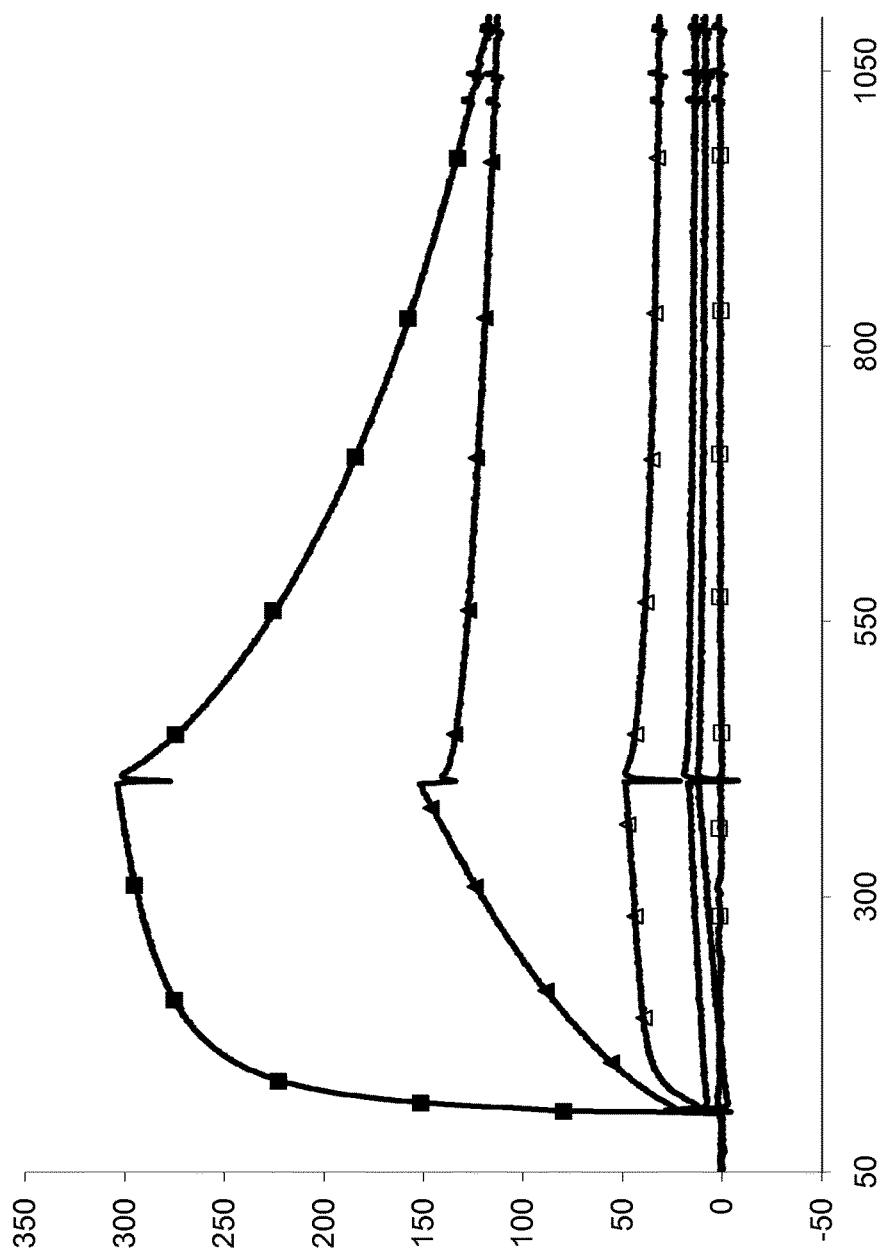
FIG. 4 shows the result of a BIACORE analysis of polypeptide variants; sensorgrams obtained after sequential injection of $His_6$-Z04777 (filled rectangles), $His_6$-Z04687 (filled triangles), $His_6$-Z04665 (open triangles), $His_6$-Z04674 (black line), $His_6$-Z04781 (grey line) and running buffer (open rectangles) over immobilized Dynazyme. Response (in RU) was plotted against time (s).

The interactions between 12 $His_6$-tagged monomeric Z variants selected according to the invention and Dynazyme were analyzed in a BIACORE instrument (GE Healthcare). The target protein was immobilized in a flow cell on the carboxylated dextran layer of a CM5 chip surface (GE Healthcare). The immobilization was performed using amine coupling chemistry according to the manufacturer's protocol and using acetate pH 5.5. One flow cell surface on the chip was activated and deactivated for use as blank during analyte injections. The analytes, i.e. polypeptide variants diluted in HBS-EP running buffer (GE Healthcare) to a final concentration of 10 µM, were injected in random order in duplicates at a flow-rate of 10 µl/minute for 5 minutes. After 10 minutes of dissociation, the surfaces were regenerated with one injection of 0.05% SDS. The results were analyzed in BiaEvaluation software (GE Healthcare). Curves of the blank surface were subtracted from the curves from the ligand surfaces. The analysis showed an interaction for 5 of the polypeptide variants to the immobilized Dynazyme, as outlined in FIG. 4.

Example 5—Comparative Study of Chemical Synthesis of a Polypeptide of a Population According to the Invention Summary In the experiments making up this example, solid phase peptide synthesis (SPPS) of polypeptides of the populations according to the invention is described, and compared to synthesis of a polypeptide based on the original scaffold. The mutations introduced at four positions, i.e. [N23T], [A42S], [A46S] and [A54S], allowed for using an alternative synthesis strategy with pseudoproline precursors with the simplified abbreviation Fmoc-Xxx-Yyy-OH. Using pseudoprolines in three or four of the positions described above, it is possible to synthesize full length molecules with the sequences:

SEQ A:
(SEQ ID No. 3)
maESEKYAKEMR NAYWEIALLP NLTNQQKRAF IRKLYDDPSQ

SSELLSEAKK LNDSQAPK (wherein ma designates mercaptoacetyl coupled to the N-terminus of the polypeptide); and SEQ B:
(SEQ ID No. 4)
AEAKYAKEMW IAWEEIRNLP NLNGWQMTAF IAKLLDDPSQ

SSELLSEAKK LNDSQAPKC;

whereas standard synthesis failed to produce the peptide with SEQ A.

Standard synthesis of SEQC: AENKFNKEMW IAWEEIRNLP NLTGWQMTAF IASLLDDPSQ SANLLAEAKK LNDAQAPK (SEQ ID No. 5), which is similar to SEQ B but contains the original scaffold amino acids, resulted in a very impure preparation and in a low peptide yield.

The introduction of novel serine or threonine residues also enables the use of isoacyl dipeptides, which is an alternative to pseudoprolines for increasing the synthetic efficiency by reducing aggregation during peptide synthesis (Sohma et al, Tetrahedron Lett. 47:3013, 2006). Several such building blocks are available from Novabiochem of Merck Biosciences AG.

Rationale

Peptide synthesis of the HER2 binding molecule $Z_{HER2:342}$ (disclosed in WO 2005/003156 as $Z_{HER2:107}$, and sometimes also called Z00342), as well as coupling of DOTA to the N-terminus for this molecule is possible and described in the literature (Orlova A et al (2006) Cancer Research 67:2178-2186). However, a huge variation in peptide yield after synthesis was observed. The difficulties to reproducibly synthesize the peptide can be related both to the length of the peptide as well as the primary amino acid sequence. In addition, long peptides with the reactive groups of the amino acid side chains still protected may generate unfavorable secondary structures, e.g. beta sheets, which can disturb solid phase peptide synthesis (Quibell M and Johnson T in Fmoc Solid Phase Peptide Synthesis-A Practical Approach, W. C. Chan, P. D. White Eds, Oxford University Press 2000:115-135). One way to prevent secondary structure formation during peptide synthesis is the use of pseudoprolines. Pseudoprolines, with the simplified abbreviation Fmoc-Xxx-Yyy-OH, can be used if the amino acid Yyy is serine, threonine or cysteine. These pseudoprolines display a closed proline-like structure with the side chain linked to the backbone, and can be converted into the normal amino acid structure by acid treatment (Haack T and Mutter M (1992) Tetrahedron Lett 33:1589-1592). Pseudoprolines are commercially available for 14 amino acids in position Xxx (all naturally occurring amino acids except Arg, Cys, His, Met, Pro, Thr) together with serine or threonine in position Yyy.

The parent molecule $Z_{HER2:342}$ has no threonine and cysteine in the primary sequence. Serine is only found in positions 33, 39 and 41. A pseudoproline precursor is only available for serine 41 ($Q^{40}$-$S^{41}$) For the two other serines, the amino acid in position Xxx prevents the use of pseudoproline, since there are no precursors available ($R^{32}$-$S^{33}$ and $P^{38}$-$S^{39}$).

The mutations introduced in the polypeptides comprised in the population according to the invention are aimed to, but not restricted to, facilitate peptide synthesis. Especially the mutations in position 23, 42, 46 and 54, i.e. [N23T], [A42S], [A46S] and [A54S] may have the capacity to solve two of the identified problems in SPPS: they allow the use of pseudoprolines and the critical region around amino acid positions 21 to 26 is changed in position 23 by replacing asparagine with threonine.

Synthesis Strategy 1

The amino acid sequence SEQ A was assembled on an Fmoc-Lys(Boc)-Wang polystyrene resin in a fully automated peptide synthesizer. This resin is highly suitable for the formation of peptides with the Fmoc-strategy. 57 amino acids (with appropriate side-chain protection) were coupled onto the resin. In the last step, coupling of S-trityl-protected mercaptoacetic acid was performed manually.

Step 1: Solid Phase Peptide Synthesis

The Fmoc-Lys(Boc)-Wang polystyrene resin was transferred into an SPPS reactor with a stirrer. Synthesis was then started with Fmoc deprotection of the resin, followed by a coupling procedure with Fmoc-Pro-OH according to the general description given below. This step was again followed by an Fmoc deprotection and subsequent coupling of the amino acid derivatives according to the sequence. After final washings of the resin with isopropylether (IPE), the peptide resin was dried in a desiccator under reduced pressure.

Both standard Fmoc peptide synthesis and synthesis using pseudoprolines in four positions were performed. For standard peptide synthesis, only Fmoc-amino acids were used. For the alternative peptide synthesis, apart from Fmoc-amino acids the following pseudoprolines were used: Fmoc-Leu-Thr-OH in position 22-23, Fmoc-Ser-Ser-OH in position 41-42, Fmoc-Leu-Ser-OH in position 45-46 and Fmoc-Asp-Ser-OH in position 53-54.

Fmoc Deprotecting Procedure

The resin was also treated with 20% piperidine in N-methyl-2-pyrrolidone (NMP) in order to achieve the cleavage of the N-α-Fmoc protecting group. The washing of the resin was then performed with NMP.

Coupling Procedure

Automated coupling of the amino acid derivates Pro57 to Glu1. Up to 3 eq of the Fmoc-AA derivative were dissolved in NMP. For the coupling, 2-(1H-benzotriazole-1-yl)-1,1,3,3-tetramethyluronium tetrafluoroborate (TBTU) in dimethylformamide (DMF) and sym.-collidine (2,4,6-trimethylpyridine) in NMP were added. The resulting solution was mixed at room temperature before it was poured onto the resin. NMP was used as solvent. After a coupling time of at least 15 minutes at 60° C., the resin was washed with NMP.

After each coupling procedure, a repetition of the coupling with 2-(1H-7-azabenzotriazol-1-yl)-1,1,3,3-tetramethyluronium tetrafluoroborate (TATU) in DMF as coupling reagent and with dichloroethane as solvent takes place automatically, followed by acetic anhydride capping.

Step 2: Coupling of Mercaptoacetic Acid

Acylations were performed with 5 molar equivalents amino acid, 2-(1H-benzotriazol-1-yl)-1,1,3,3-tetramethyluronium hexafluorphosphate (HBTU) and 1-hydroxybenzotriazole (HOBt) and 10 equivalents N-ethyldiisopropylamine (DIEA, from Lancaster Synthesis, Morecambe, England). S-trityl-mercaptoacetic acid was from AnaSpec Inc (San Jose, Calif., USA).

Step 3: Cleavage from the Resin Including Cleavage of the Remaining Protection Groups The peptide resin was treated with trifluoroacetic acid (TFA) in the presence of purified water, ethanedithiol (EDT), and triisopropylsilane (TIS). After approx. 2 hours of cleavage time at room temperature, the reaction mixture was cooled to approx. 0° C., and ammonium iodide and dimethyl sulfide are added to reduce oxidized methionine. After an additional 60 min cleavage time at approx. 0° C., the formed iodine was reduced with ascorbic acid. After filtering off the product, it was precipitated in IPE in the cold, filtered off again, washed with IPE, and dried under reduced pressure.

Purity Analysis by HPLC

The purity of the 58 amino acid long peptides and some intermediates was determined by reversed phase HPLC using a Vydac 218 TP54 (5 μm, 250×4.6 mm) column and 0.1% TFA, 1% acetonitrile in $H_2O$ and 0.1% TFA in acetonitrile as solvent A and B respectively. The column oven temperature was set to 35° C. The column was eluted either with a gradient of 15 to 45% solvent B in 30 minutes or with a gradient from 20 to 50% B in 30 minutes. UV detection was at 220 nm. The purity was calculated by area normalization.

Results

Figure 5A:
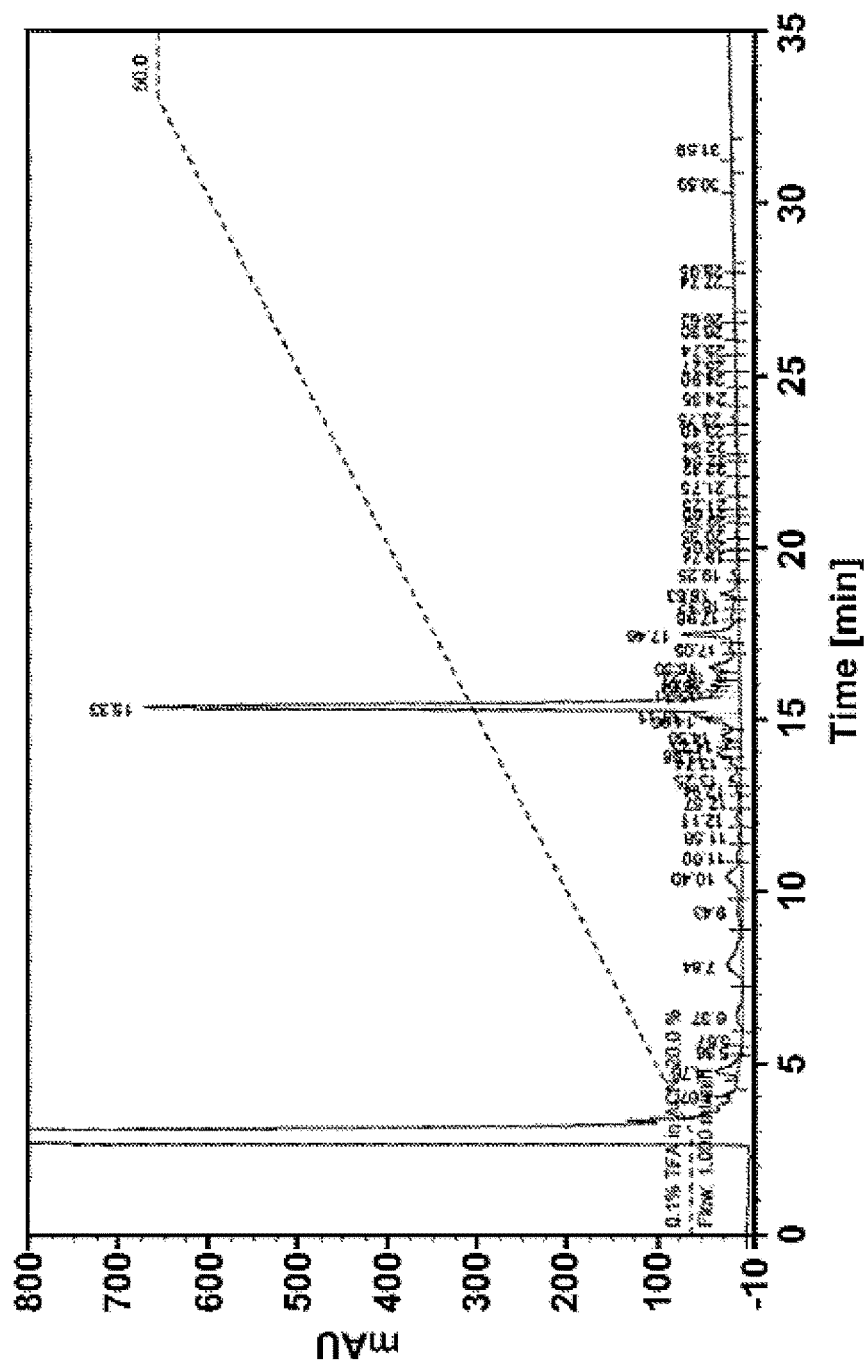
FIG. 5A and FIG. 5B show analytical HPLC elution profiles for polypeptides with the sequence maESEKYAKEMR NAYWEIALLP NLTNQQKRAF IRKLYDDPSQ SSELLSEAKK LNDSQAPK (SEQ ID No. 3) at the synthesis stage of amino acid residues 18 to 58. A) Synthesis performed on polystyrene resin using pseudoprolines in positions 22-23, 41-42, 45-46 and 53-54. B) Standard peptide synthesis on polystyrene resin without pseudoprolines.
Figure 5B:
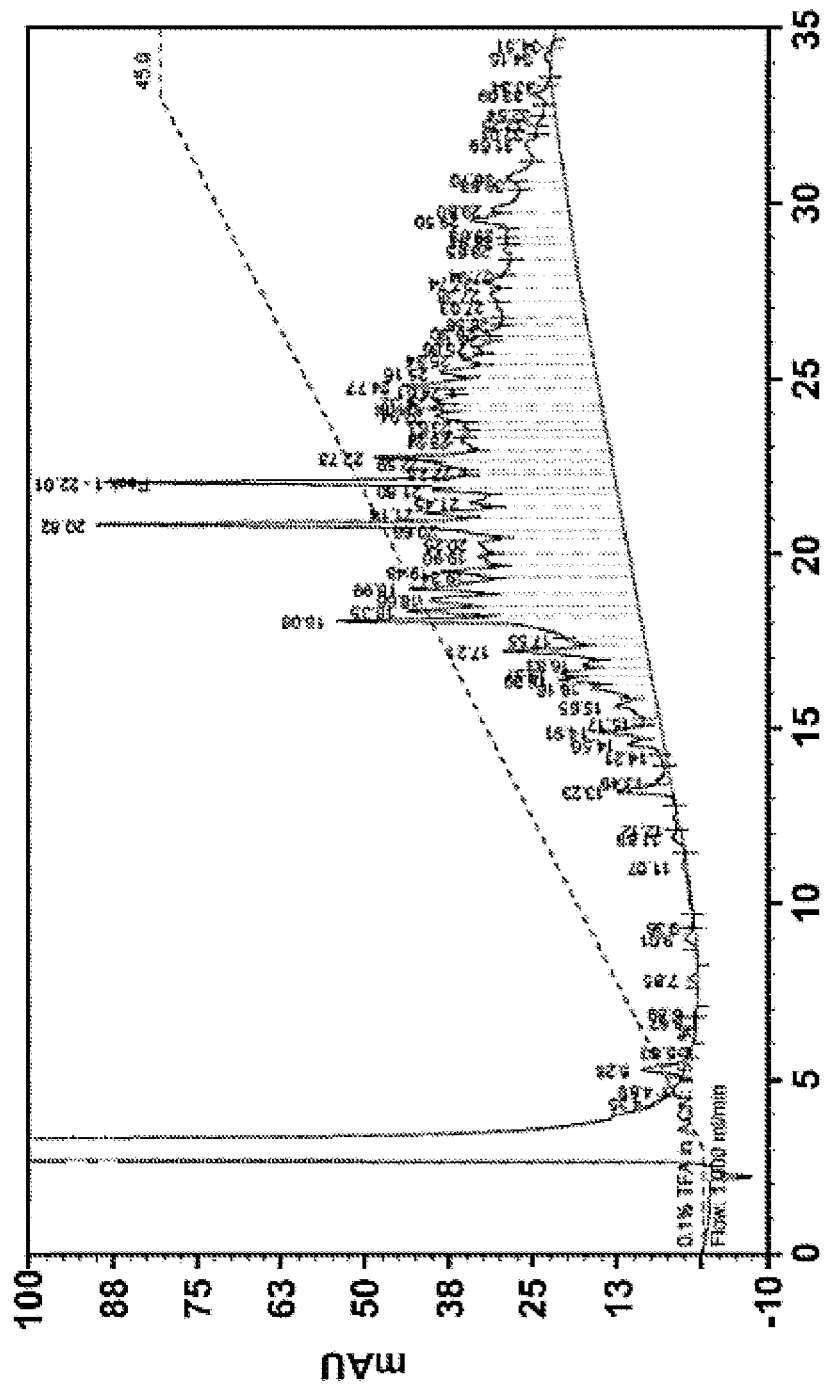
Figure 6A:
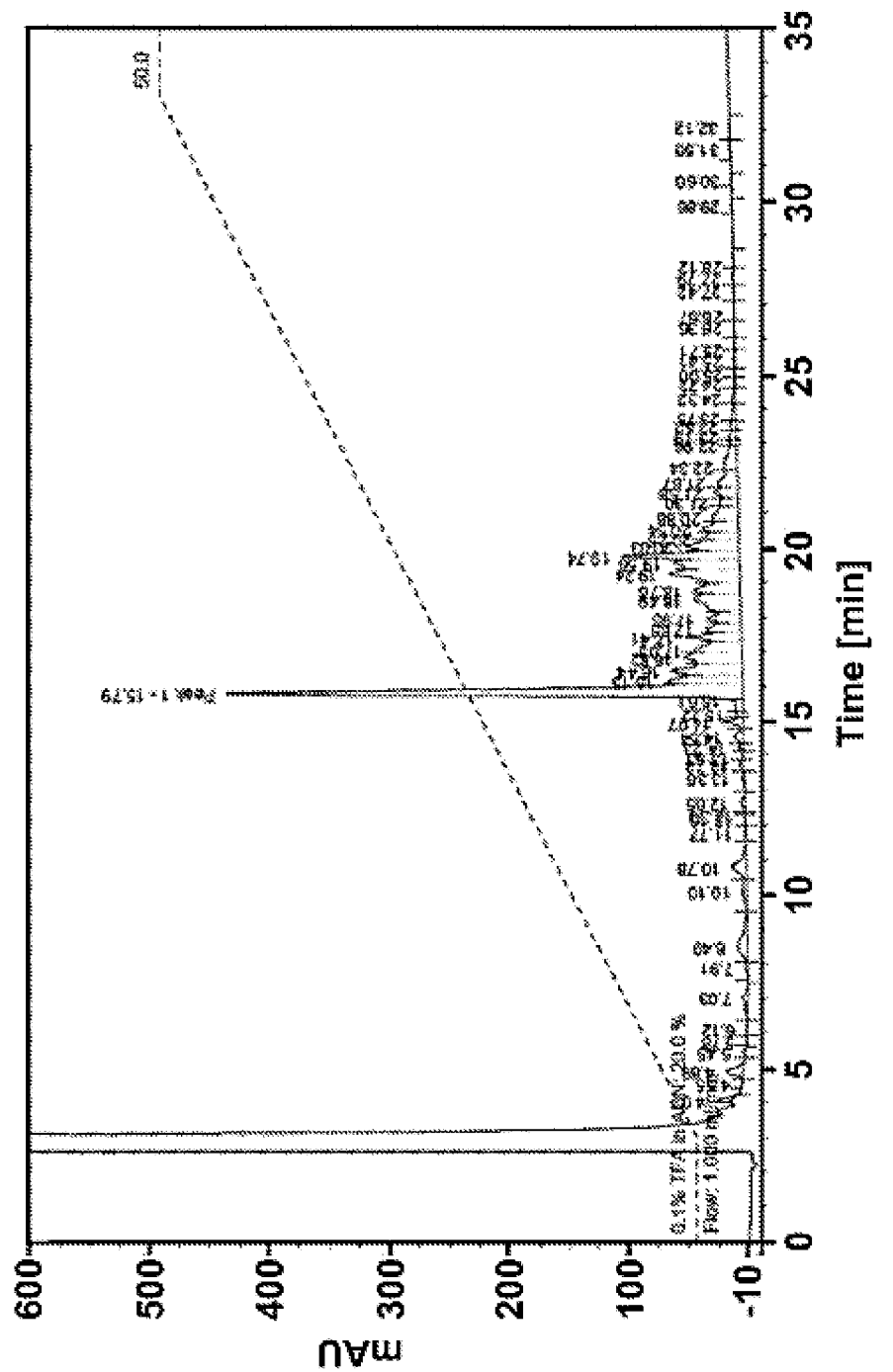
FIG. 6A and FIG. 6B show analytical HPLC elution profiles for polypeptides with the sequence maESEKYAKEMR NAYWEIALLP NLTNQQKRAF IRKLYDDPSQ SSELLSEAKK LNDSQAPK (SEQ ID No. 3) at the synthesis stage of amino acid residues 1 to 58 (A) and 10 to 58 (B). A) Synthesis performed on polystyrene resin using pseudoprolines in positions 22-23, 41-42, 45-46 and 53-54. B) Standard peptide synthesis on polystyrene resin without pseudoprolines.
Figure 6B:
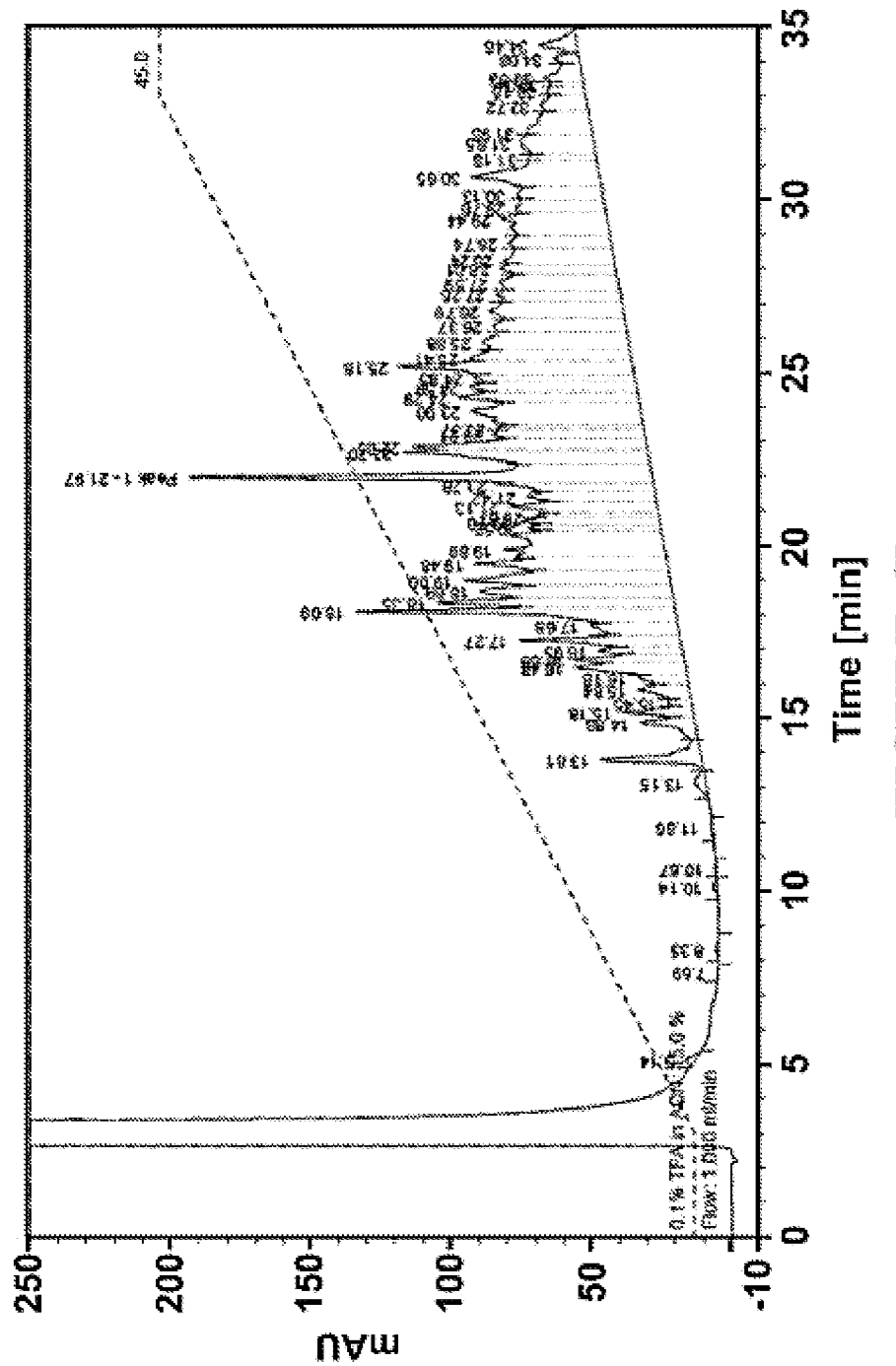

The yield and purity of the molecule with the sequence SEQ A, synthesized with or without the use of pseudoprolines, were analyzed by analytical reversed phase chromatography. In order to follow the progress of the synthesis, a small portion of synthesis resin was taken after several coupling steps and analyzed for the presence, purity and yield of the desired peptide intermediate. FIG. 5A and FIG. 5B show the HPLC analysis of the 41 amino acid long peptide intermediate (amino acid 18-58). At this stage of the peptide synthesis, one clear and predominant peptide peak with the correct sequence (RT=15.33 min, yield 49%) was identified if the synthesis was performed using pseudoprolines (FIG. 5A). Standard Fmoc synthesis, however, resulted in a huge number of small peptide peaks and two main peaks with similar size, but low yield. One of this two peaks (RT=20.82 min) was identified as the peptide intermediate with the correct sequence (aa 18-58) (FIG. 5B). The full length peptide (amino acids 1-58) was obtained only if the synthesis was performed using pseudoprolines. FIG. 6A shows a single product peak with a yield of the final peptide of 26%. Standard Fmoc-synthesis, however, failed to produce the final peptide product. Analysis of the 49 amino acid long intermediate (amino acid 10-58) from the standard synthesis revealed that the desired intermediate could not be detected and the synthesis was aborted (FIG. 6B).

Synthesis Strategy 2

Two molecules were assembled using the Fmoc-strategy on a fully automated peptide synthesizer with an integrated microwave oven.

The 59 amino acid residues of SEQ B, based on the inventive scaffold sequence, were assembled (with appropriate side chain protection) on an Fmoc-Cys(Trt)-Wang LL polystyrene resin.

The 58 amino acid residues of SEQ C, based on the original AFFIBODY molecule scaffold, were assembled (with appropriate side chain protection) on an Fmoc-Lys (Boc)-Wang LL polystyrene resin.

The Wang resin LL is highly suitable for the formation of peptides with the Fmoc strategy.

Step 1: Solid Phase Peptide Synthesis

The polystyrene resin was automatically transferred into an SPPS reaction vessel by the synthesizer (Liberty, CEM Corporation, NC USA). Synthesis was then started with Fmoc deprotection of the resin, followed by a coupling procedure with the next Fmoc-protected amino acid (Fmoc-AA) according to the general description given below. This step was again followed by an Fmoc deprotection and subsequent coupling of the amino acid derivatives according to the sequence. After final washings of the resin with dichloromethane (DCM), the peptide resin was dried under reduced pressure. The entire peptide SEQ C was made by standard Fmoc peptide synthesis, whereas pseudoprolines were used at positions in SEQ B where this was enabled by the improvements done to the scaffold. The following pseudoprolines were used: Fmoc-Ser-Ser-OH at position 41-42, Fmoc-Leu-Ser-OH at position 45-46 and Fmoc-Asp-Ser-OH at position 53-54.

Fmoc Deprotecting Procedure

The resin was treated with 5% piperazine in NMP, with microwave irradiation, in order to achieve the cleavage of the N-α-Fmoc protecting group. The washing of the resin was then performed with NMP.

Coupling Procedure

Automated coupling of the amino acid derivatives Cys59 to Ala1 (for SEQ B) and Lys58 to Ala1 (for SEQ C). Up to 5 equivalents of the Fmoc-AA were dissolved in NMP. For the coupling, O-(benzotriazole-N,N,N',N'-tetramethyluronium hexafluorophosphate (HBTU) and N-hydroxybenzotriazole (HOBt) in dimethylformamide (DMF), N,N'-diisopropylethylamine (DIPEA) in NMP were added to the resin at a molar ratio of 1:1:1:2 (AA/HBTU/HOBt/DIPEA). The mixture was agitated by bubbling nitrogen gas through the bottom of the reaction vessel. After a coupling time of at least 5 minutes at 75-80° C. with added energy using microwave irradiation, the resin was washed with NMP.

After each coupling procedure, an automatic acetic anhydride capping was performed.

Step 2: Cleavage from the Resin Including Cleavage of the Remaining Protection Groups The peptide resin was treated with trifluoroacetic acid (TFA) in the presence of purified water, ethanedithiol (EDT), and triisopropylsilane (TIS). After approx. 2 hours of cleavage at room temperature, the cleavage mixture was filtered and the resin rinsed with neat 95% TFA/water. The filtrate was slowly added to cooled methyl tert-butyl ether (MTBE). The precipitate was centrifuged and the MTBE removed. The solid was resuspended in ether and the operation repeated a total of three times. After the last removal of ether, the solid was resuspended in 0.1% TFA/water, the remaining ether was left to evaporate, and the solution was frozen before lyophilisation.

Purity and Mass Analysis by HPLC-MS

The purity of the peptides was determined by high performance liquid chromatography and on line mass spectrometry (HPLC-MS) using an Agilent 1100 HPLC/MSD equipped with electro spray ionization (ESI) and a single quadropol. The HPLC was run using a Zorbax 300SB C18 (3.5 μm, 150×4.6 mm) column and 0.1% TFA/water and 0.1% TFA/acetonitrile (ACN) as solvent A and B respectively. The column oven temperature was set to 30° C. The column was eluted with a gradient of 15 to 55% solvent B in 40 minutes. UV detection was at 220 nm. The purity was calculated by area normalization. The software used for the mass analysis and evaluation was ChemStation Rev. B.02.01. (Agilent).

Results

Figure 7A:
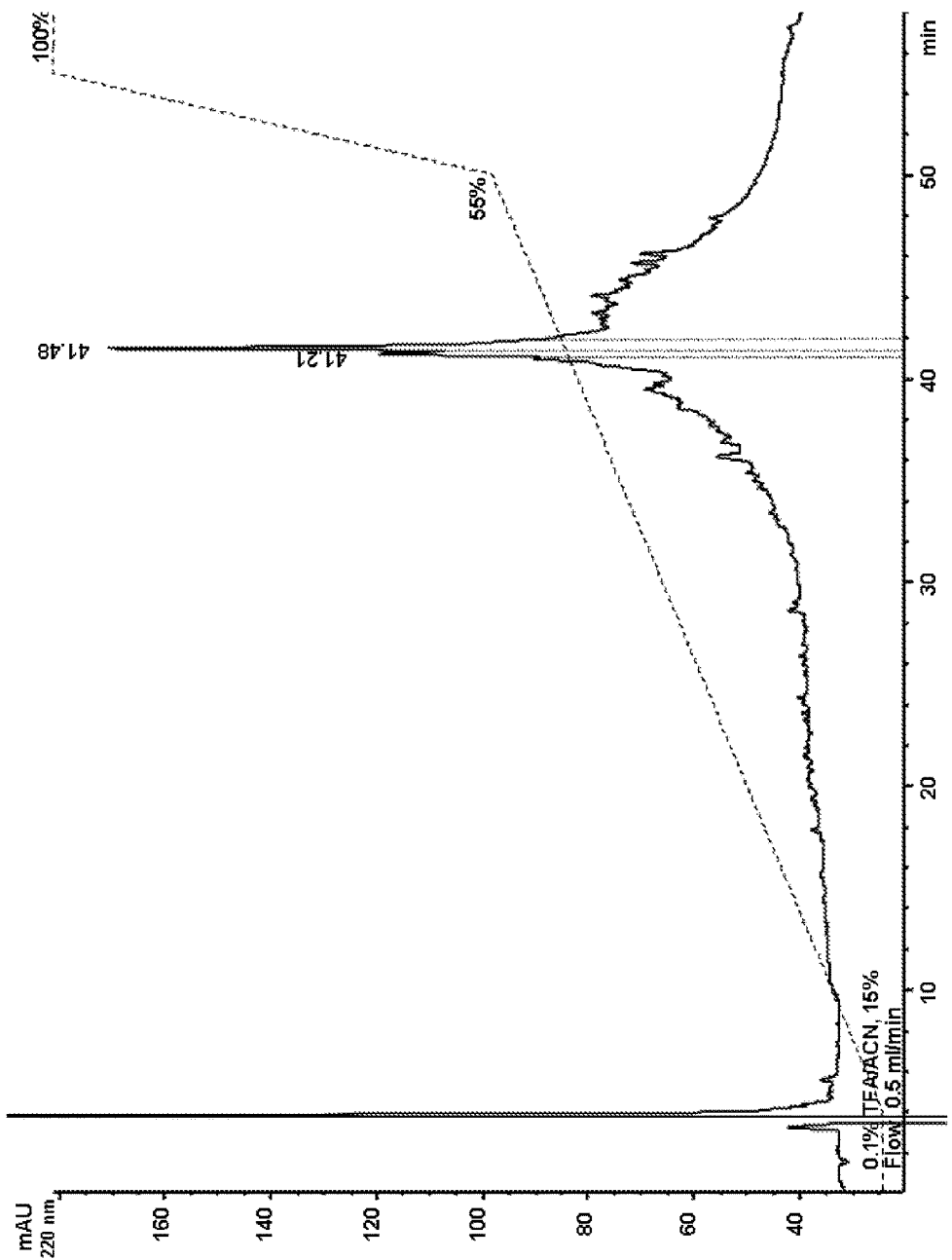
FIG. 7A and FIG. 7B show analytical HPLC elution profiles for polypeptides with the sequence A) AEAKYAKEMW IAWEEIRNLP NLNGWQMTAF IAKLLDDPSQ SSELLSEAKK LNDSQAPKC (SEQ ID No. 4 according to the invention) and B) AENKFNKEMW IAWEEIRNLP NLTGWQMTAF IASLLDDPSQ SANLLAEAKK LNDAQAPK (SEQ ID No. 5 for comparison).

The yield and purity of the molecules SEQ B and SEQ C was analyzed by analytical reversed phase chromatography. The full length peptides were obtained in both syntheses, however with a much larger yield for SEQ B. FIG. 7A shows, for SEQ B, a main product peak (RT=41.48 min) with the expected mass and a yield of the final peptide of 15%. An additional peak (RT=41.21 min) with a yield of 8% was found to have a mass that was 72 Da higher than the expected mass of the full length product. This is believed to be due to a side reaction on the Cys59 amino acid residue. Depending of the type of side reaction, this can occur during the synthesis or during the cleavage of the peptide from the resin. By optimising the synthesis and/or the cleavage protocol, this side reaction could be minimized and the yield thereby increased, in this case up to a total yield of 23%.

Figure 7B:
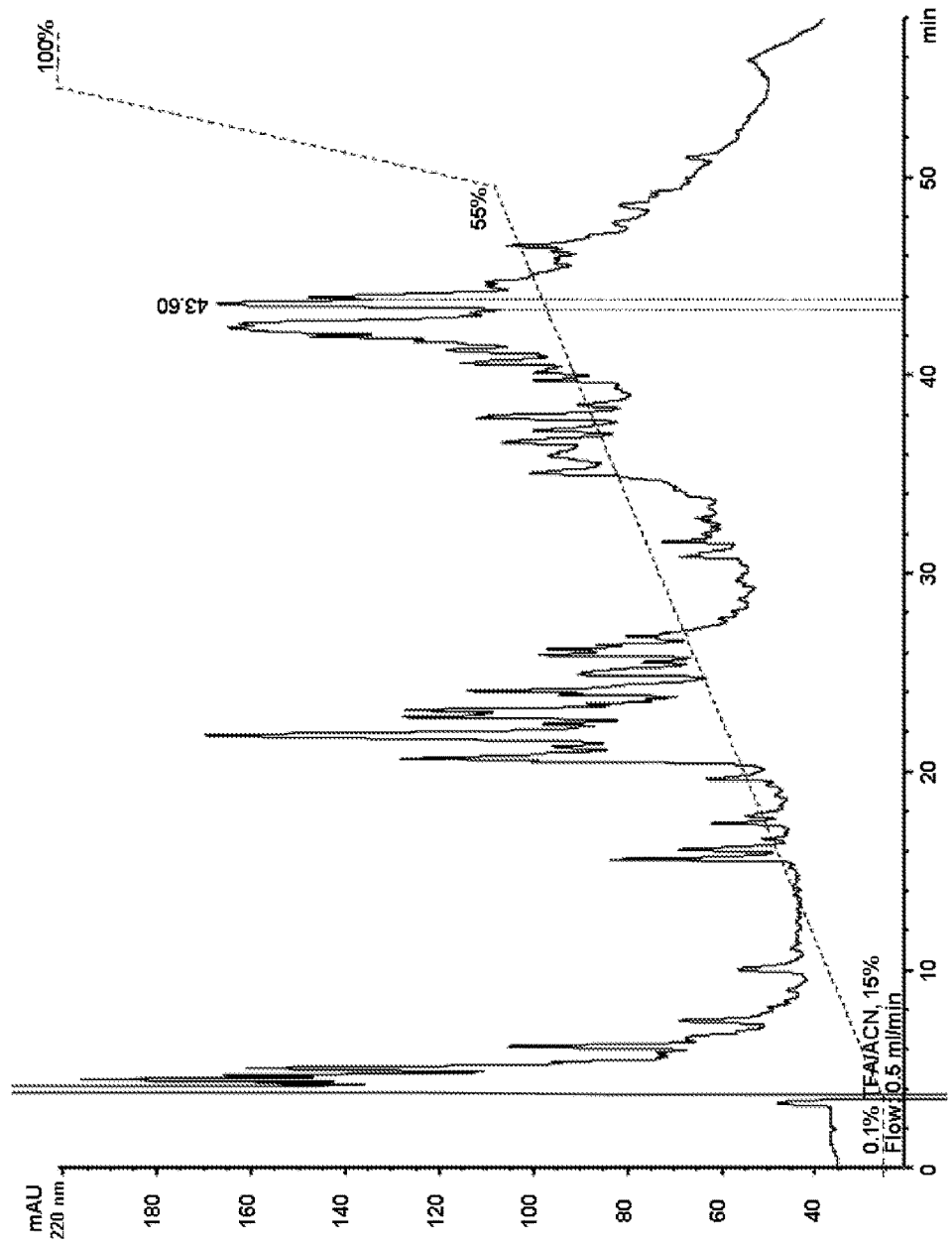

Standard Fmoc-synthesis of SEQ C, however, resulted in a large number of small peptide peaks (FIG. 7B). One of the main peaks (RT=43.60 min) was identified as the full length peptide with the expected mass. The yield of this product was 4%.

Example 6—Immunogenicity of Original and Inventive Polypeptide Variants

Summary

In this example, the immunogenicity of one original and one inventive polypeptide variant was compared in vivo. Dimeric molecules were administered to rats, and the specific antibody responses were determined in an Anti-Drug Antibody (ADA) assay. The molecule with the introduced scaffold mutations according to the invention displays a lower and delayed antibody response compared to the original Z variant.

Cloning and Production of Polypeptides

Two Taq-polymerase specific binding polypeptides fused to the albumin binding domain ABD035 (Jonsson et al (2008) Protein Eng Des Sel 8:515-27) were used in the study:

1. (Z01154)$_2$-ABD035: original scaffold
2. (Z03229)$_2$-ABD035: inventive scaffold PCR amplified and hybridized fragments of Z01154 and Z03229 with Accl-overhangs were cloned as dimers in the Accl digested pET (Novagen) derived expression vectors pAY492 and pAY1450 respectively. The resulting vectors were digested with AccI-NotI and ligated with ABD035 fragments that had been PCR amplified with AccI and NotI overhangs, generating the constructs pAY1827 (encoding MGSSLQ-[Z01154]-[Z01154]-VD-[ABD035] (SEQ ID No. 40)) and pAY2292 (encoding MGSSLQ-[Z03229]-[Z03229]-VD-[ABD035] (SEQ ID No. 41)). The plasmids were transformed into competent *E. coli* BL21(DE3) cells and proteins were produced by fermentation, essentially as described in Example 3. Pelleted cells were suspended in [25 mM Tris-HCl, 200 mM NaCl, 1 mM EDTA, 25 U/ml BENZONASE (Merck, #1.01654.0001), pH 8.0] and disrupted by sonication on ice. The clarified supernatants were loaded onto a column packed with CNBr-activated Sepharose (GE Healthcare, #17-0981-03) coupled in-house with human serum albumin. The column was pre-equilibrated in 1×TST [25 mM Tris-HCl, 200 mM NaCl, 1 mM EDTA, 0.05% Tween 20, pH 8.0]. After sample application, washing was performed with 1×TST followed by 5 mM $NH_4Ac$ pH 5.5 until no reduction of the $Abs_{280}$ signal was observed. Bound proteins were eluted with 0.5 M HAc, pH 2.8. The eluted samples were supplemented with acetonitrile to a final concentration of 2% and further purified by reverse phase chromatography on a Resource RPC column (GE Healthcare, #17-1182-01). [2% acetonitrile, 0.1% TFA in water] was used as running buffer and samples were eluted using a linear gradient of 0-50% of [80% acetonitrile, 0.1% TFA in water] over 25 column volumes. Buffer exchange to [5 mM sodium phosphate, 150 mM NaCl, pH 7.2] was performed using a HiPrep 26/10 Desalting column (GH Healthcare, #17-5087-01). Sample purity was verified by SDS-PAGE and LC/MS analysis as described in Example 3. Endotoxin traces were removed on an AffinityPak Detoxi-Gel endotoxin removing gel (Thermo, #20344) according to the manufacturer's instructions. No endotoxins were detected in gel-clot LAL tests performed by APL (Apoteket Produktion & Laboratorier AB, Sweden). The samples were free of soluble aggregates as verified by size-exclusion chromatography carried out on a Superdex 75 10/300 column (GE Healthcare, #17-5174-01) using 1×PBS as running buffer, a flow rate of 0.5 ml/min and a sample volume of 100 μl with a concentration of 1 mg/ml.

Administration and Sampling Schemes

The animal study was performed at Agrisera AB (Vännäs, Sweden) with permission from the local animal ethics committee. Female Sprague Dawley rats divided into three groups were injected subcutaneously with $(Z01154)_2$-ABD035, $(Z03229)_2$-ABD035 or a buffer control as outlined in Table 9. Injections were given at days 0, 4, 7, 14, 21 and 28. 250 μl blood samples were collected from each animal on day −1 (pre-serum) and on days 6, 13, 20 and 35. All animals were sacrificed on day 35. Collected blood samples were left to coagulate over night at 4° C. and obtained sera were stored at −20° C. until analysis.

TABLE 9

Sample administration scheme

| Group | No. of animals | Molecule | Means of administration | mg/ animal/ injection | ml/animal/ injection |
|---|---|---|---|---|---|
| 1 | 8 | $(Z01154)_2$-ABD03 | s.c. | 0.125 | 0.1 |
| 2 | 8 | $(Z03229)_2$-ABD035 | s.c. | 0.125 | 0.1 |
| 3 | 4 | Buffer control: 5 mM sodium phosphate, 150 mM NaCl, pH 7.2 | s.c. | — | 0.1 |

Anti-Drug Antibody (ADA) Assay

To analyze the presence of anti-$(Z01154)_2$-ABD035 and anti-$(Z03229)_2$-ABD035 antibodies, three types of ELISA analyses were performed. All samples were initially screened for the presence of reacting antibodies followed by a confirmatory assay to verify specificity. Serum samples with specific antibodies against Z variants were subsequently titrated to quantify the titer of anti-$(Z01154)_2$-ABD035 and anti-$(Z03229)_2$-ABD035 antibodies.

For screening of serum samples, ELISA plates (96-well, half-area plates, Costar, #3690) were coated over night with $(Z01154)_2$-ABD035 or $(Z03229)_2$-ABD035 diluted in coating buffer (Sigma, # C3041) to a final concentration of 2 μg/ml. 50 μl of the coating solution was added per well and plates were incubated over night at 4° C. The plates were washed twice manually with deionized water and subsequently blocked for 2 hours with 100 μl/well of PBS-Casein (PBS with 0.5% Casein (Sigma, #8654)). The blocking solution was removed and serum samples (50 μl/well) diluted 1:50 in blocking buffer were added. After 1.5 hour of incubation at RT, plates were washed in an automated ELISA washer (Scanwasher 300, Scatron) with PBST (PBS with 0.05% Tween 20 (Acros Organics, #233362500)). To detect rat antibodies against Z variants, 50 μl per well of HRP-conjugated anti-rat IgG (Southern Biotech, #3050-05), diluted 1:6000 in PBS-Casein were added. After 1 hour of incubation, the plates were washed as described above and 50 μl/well of substrate solution (IMMUNOPURE TMB, Pierce, #34021) were added. The plates were incubated at RT in the dark, and color development was stopped after 15 minutes with 50 μl/well of 2 M $H_2SO_4$ (VWR, #14374-1). Plates were read at 450 nm in an ELISA reader (Victor[3], Perkin Elmer).

The ELISA method described above was also used for the confirmatory and titration ELISA assays, but with some alterations. For the confirmatory assay, serum samples were diluted 1:50 in PBS-Casein or in PBS-Casein including 1 μg/ml of respective polypeptide variant. Serum samples with a reduction of the OD signal of 45% or more were considered to contain specific antibodies against Z variants. For the titration assay, serum samples were diluted 1:50 in PBS-Casein and then in series of 2-fold or 5-fold dilutions until they crossed the plate-specific cut point to allow a titer value to be calculated for the sample.

During assay development the following key parameters were determined:
Minimum dilution: 1:50
Non specific background (NSB): $OD_{450}$ of a pool of normal rat sera (Sprague Dawley rats, Scanbur) used as dilution matrix and included on each plate throughout the analysis Assay cut point: mean $OD_{450}$ of normal rat sera from 30 individuals plus 1.645 times standard deviations of the mean. A value of 0.11 was obtained for both $(Z01154)_2$-ABD035 and $(Z03229)_2$-ABD035.

Normalisation factor. Assay cut point divided by the mean $OD_{450}$ of the NSB: 1.87 and 1.86 for $(Z01154)_2$-ABD035 and $(Z03229)_2$-ABD035, respectively During sample analysis, the plate specific cut point was then determined as: Mean $OD_{450}$ of plate specific NSB, multiplied by the normalisation factor.

Rat serum (hyperimmunised Sprague Dawley rats, Agrisera) confirmed to contain antibodies against the two polypeptide variants were used for preparing positive control (PC) samples included on each plate throughout the analysis: HighPC: positive control serum diluted 1:4 in matrix before minimum dilution in PBS-Casein. This PC has OD values high above the assay/plate cut point. LowPC: Positive control serum diluted 1:300 in matrix before minimum dilution in PBS-Casein. This PC has OD values that fall just above the assay/plate cut point.

The LowPC and HighPC values were used to prepare the Titer quality controls LoQC1-5 and HiQC1-5). The LowPC and HighPC were diluted 1:50 in PBS-Casein to obtain LoQC1 and HiQC1 respectively. These were then further diluted in PBS-Casein to obtain LoQC2 (1:100), LoQC3 (1:200), LoQC4 (1:400) and LoQC5 (1:800), and HiQC2 (1:250), HiQC3 (1:1250), HiQC4 (1:6250) and HiQC5 (1:31250), respectively.

The titer values were calculated using GraphPad Prism 5 (GraphPad Software Inc). Briefly, $OD_{450}$ values were plotted against log dilution and the titer of the sample was defined as the log dilution at the plate specific cut point.

Results

The in vivo comparison between original $((Z01154)_2$-ABD035) and inventive $((Z03229)_2$-ABD035) molecules showed that the inventive molecule was less immunogenic. The response varied considerably between individuals and increased over time. The titer could be determined in three individuals that received the original molecule compared to two individuals that received the inventive molecule. The actual titer was also lower in the group that received the inventive molecule (Table 10). The reason for seeing few animals develop an antibody response may be due to the fused ABD molecule, which previously has been shown to reduce immunogenicity of a fused polypeptide (see e.g. WO 2005/097202).

TABLE 10

Immune responses in rats given an original or an inventive polypeptide variant

| | Group 1 $(Z01154)_2$-ABD035 n = 8 | | Group 2 $(Z03229)_2$-ABD035 n = 8 | | Group 3 Buffer control n = 4 | |
|---|---|---|---|---|---|---|
| Time (days) | Specific response (no. of animals) | Titer Mean ± SD | Specific response (no. of animals) | Titer Mean ± SD | Specific response (no. of animals) | Titer Mean ± SD |
| −1 | 0 | — | 0 | — | 0 | — |
| 6 | 0 | — | 0 | — | 0 | — |
| 13 | 1 | 2.9 | 0 | — | 0 | — |
| 20 | 2 | 3.4 (±1.0) | 1 | 2.1 | 0 | — |
| 27 | 3 | 2.7 (±1.0) | 1 | 2.4 | 0 | — |
| 35 | 2 | 3.4 (±1.3) | 2 | 2.8 (±0.1) | 0 | — |

The invention claimed is:

1. A polypeptide having affinity for a predetermined target, comprising the first scaffold amino acid sequence (SEQ. ID. No. 1)
EXXXAXXEIX XLPNLTXXQX XAFIXKLXDD PSQSSELLSE

AKKLNDSQ wherein each X corresponds to a randomizable amino acid residue in a second polypeptide based on an original scaffold amino acid sequence and wherein said second polypeptide has affinity for said predetermined target.

2. The polypeptide according to claim 1, wherein the first scaffold amino acid sequence comprises (SEQ. ID. No. 2)
AKYAK EXXXAXXEIX XLPNLTXXQX XAFIXKLXDD PSQSSELLSE

AKKLNDSQ wherein each X corresponds to a randomizable amino acid residue in a second polypeptide based on an original scaffold amino acid sequence and wherein said second polypeptide has affinity for said predetermined target.

3. A polypeptide according to claim 1, wherein said first scaffold amino acid sequence is derived from SpA.

4. The polypeptide according to claim 1 comprising additional amino acid residues.

5. The polypeptide according to claim 4 comprising additional amino acid residues at the C-terminus of said polypeptide.

6. The polypeptide according to claim 4, wherein said additional amino acid residues are added for the purpose of binding, production, purification, stabilization, coupling or detection of the polypeptide.

7. The polypeptide according to claim 4, wherein said additional amino acid residues constitute one or more polypeptide domain(s).

8. The polypeptide according to claim 7, wherein said one or more polypeptide domain(s) has a function selected from the group of a binding function, an enzymatic function, a metal ion chelating function and a fluorescent function, or mixtures thereof.

9. The polypeptide according to claim 1, further comprising a label.

10. The polypeptide according to claim 1, further comprising a therapeutic agent.

11. The polypeptide according to claim 1, wherein said target is TNF-α.

12. The polypeptide according to claim 1, wherein said target is insulin.

13. The polypeptide according to claim 1, wherein said target is taq-polymerase.

14. The fusion polypeptide comprising a polypeptide according to claim 1 as a moiety.

15. A method for production of the polypeptide of claim 1, comprising the steps of
providing a second polypeptide having affinity for a predetermined target wherein said second polypeptide is based on an original scaffold derived from SpA, and
mutating original scaffold amino acids to generate the polypeptide of claim 1 comprising the first scaffold amino acid sequence (SEQ. ID. No. 1)
EXXXAXXEIX XLPNLTXXQX XAFIXKLXDD PSQSSELLSE

AKKLNDSQ wherein each X individually corresponds to an amino acid residue which is conserved from the second polypeptide.

16. The method of claim 15, wherein the first scaffold amino acid sequence comprises (SEQ. ID. No. 2)
AKYAK EXXXAXXEIX XLPNLTXXQX XAFIXKLXDD PSQSSELLSE

AKKLNDSQ wherein each X individually corresponds to an amino acid residue which is conserved from the second polypeptide.

17. The method according to claim 15, wherein said polypeptide comprises the amino acid sequence
ELGWAIGEIG TLPNLTHQQF RAFILKLWDD PSQSSELLSE AKKLNDSQ (SEQ ID NO: 44), and
wherein said predetermined target is TNF-α.

18. The method according to claim 15, wherein said polypeptide comprises the amino acid sequence
EKYMAYGEIR LLPNLTHQQV MAFIDKLVDD PSQSSELLSE AKKLNDSQ (SEQ ID NO: 45), and
wherein said predetermined target is insulin.

19. The method according to claim 15, wherein said polypeptide comprises the amino acid sequence
EKGEAVVEIF RLPNLTGRQV KAFIAKLYDD PSQS-SELLSE AKKLNDSQ (SEQ ID NO: 46), and
wherein said predetermined target is taq-polymerase.

20. The method according to claim 15, wherein said original scaffold is derived from SpA domain B and
wherein mutating original scaffold amino acids comprises a G29A mutation, corresponding to A in position 22 in SEQ ID NO:1 and A in position 27 in SEQ ID NO: 2.

* * * * *